(12) United States Patent
Prisk et al.

(10) Patent No.: US 9,750,427 B2
(45) Date of Patent: Sep. 5, 2017

(54) MAGNETIC RESONANCE IMAGING OF VENTILATION AND PERFUSION IN THE LUNG

(75) Inventors: Gordon Kim Prisk, San Diego, CA (US); Susan Roberta Hopkins, San Diego, CA (US); Richard Bruce Buxton, La Mesa, CA (US); Rui Carlos Pereira De Sá, San Diego, CA (US); Rebecca Jean Theilmann, San Diego, CA (US); Matthew Vincent Cronin, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 207 days.

(21) Appl. No.: 13/992,231

(22) PCT Filed: Dec. 7, 2011

(86) PCT No.: PCT/US2011/063854
§ 371 (c)(1),
(2), (4) Date: Sep. 3, 2013

(87) PCT Pub. No.: WO2012/078823
PCT Pub. Date: Jun. 14, 2012

(65) Prior Publication Data
US 2013/0338489 A1  Dec. 19, 2013

Related U.S. Application Data

(60) Provisional application No. 61/420,554, filed on Dec. 7, 2010.

(51) Int. Cl.
*A61B 5/00* (2006.01)
*A61B 5/055* (2006.01)
(Continued)

(52) U.S. Cl.
CPC ............... *A61B 5/055* (2013.01); *A61B 5/08* (2013.01); *A61B 5/0813* (2013.01); *G01R 33/5601* (2013.01); *G01R 33/56366* (2013.01)

(58) Field of Classification Search
None
See application file for complete search history.

(56) References Cited

U.S. PATENT DOCUMENTS 5,694,934 A  12/1997 Edelman
6,915,151 B2  7/2005 Baumgardner et al.
(Continued)

OTHER PUBLICATIONS

Mai, V. M., Bankier, A. A., Prasad, P. V., Li, W., Storey, P., Edelman, R. R. and Chen, Q. (2001), MR ventilation-perfusion imaging of human lung using oxygen-enhanced and arterial spin labeling techniques. J. Magn. Reson. Imaging, 14: 574-579.*

(Continued)

*Primary Examiner* — Tse Chen
*Assistant Examiner* — Joanne Hoffman
(74) *Attorney, Agent, or Firm* — Perkins Coie LLP

(57) ABSTRACT

Methods, devices, and systems are disclosed for implementing a fully quantitative non-injectable contrast proton MRI technique to measure spatial ventilation-perfusion (VA/Q) matching and spatial distribution of ventilation and perfusion. In one aspect, a method using MRI to characterize ventilation and perfusion in a lung includes acquiring an MR image of the lung having MR data in a voxel and obtaining a breathing frequency parameter, determining a water density value, a specific ventilation value, and a perfusion value in at least one voxel of the MR image based on the MR data and using the water density value to determine an air content value, and determining a ventilation-perfusion ratio value that is the product of the specific ventilation value, the air content value, the inverse of the perfusion value, and the breathing frequency.

26 Claims, 12 Drawing Sheets

(51) Int. Cl.
*A61B 5/08* (2006.01)
*G01R 33/56* (2006.01)
*G01R 33/563* (2006.01)

(56) References Cited

U.S. PATENT DOCUMENTS

2006/0056691 A1 3/2006 Vaz et al.
2007/0241752 A1* 10/2007 Meersmann et al. ......... 324/307
2010/0145186 A1 6/2010 McGrath et al.

OTHER PUBLICATIONS

Vu M. Vai, Alexander A. Bankier, Pottumarthi V. Prasad, Wei Li, Pippa Storey, Robert R. Edelman, and Qun Chen, "MR Ventilation-Perfusion Imaging of Human Lung Using Oxygen-Enhanced and Arterial Spin Labeling Techniques", Journal of Magentic Resonance Imaging, 14:564-579, 2001.*
J. Yu, J. Baumgardner, M. Ishii, Z. Z. Spector, M. Fischer, J. Han, M. Itkin, D. Lipson, R. R. Rizi, "Calculation of Regional Partial Pressure of Oxygen and Ventilation / Perfusion Ratio in a Porcine Model of the Normal Lung and the Lung with Perfusion Abnormality", Proc. Intl. Soc. Mag. Reson. Med, 11, 2004.*
William R. Welch and C. Richard Tracy, "Respiratory Water Loss: A PRedictive Model", J. theor. Biol. 65:253-265, 1977.*
G. H. Mills, J. M. Wild, B. Eberle, and E. J. R. Van Beek, "FUncitonal magnetic resonance imaging of the lung", British Journal of Anaesthesia 91(1):16-30, 2003.*
Richard C. Semelka, N. Cem Balci, Kathy P. Wilber, Laurie L. Fisher, Mark A. Brown, Andres Gomez-Caminero, and Paul L. Molina, "Breath-Hold 3D Gradient-Echo MR Imaging of the Lung Parenchyma: Evaluation of Reproducibility of Image Quality in Normals and Preliminary Observations in Patients With Disease", Journal of Magnetic Resonance Imaging, 2000.*
Nilesh N. Mistry, Yi Ql, Laurence W. Hedlund, and G. Allan Johnson, "Ventilation/Perfusion Imaging in a Rat Model of Airway Obstruction", Magn Reson Med, 63(3):728-735, 2010.*
Lakeside Press, "Chapter 4, PCO2 and alveolar ventilation" 2005.*
Elizabeth Dean, "Effect of Body Position on Pulmonary Function", Physical Therapy, 5 (5) 1985.*
G. Bauman, M. Puderbach, M. Deimling, V. Jellus, C. Chefd'hotel, J. Dinkel, C. Hintze, H. Kauczor, L. Shad, "Non-Contrast-Enhanced Perfusion and Ventilation Assessment of the Human Lung by Means of Fourier Decomposition in Proton MRI", Magnetic Resonance in Medicin, 62, pp. 656-664 (2009).*
Adolphi NL, and Kuethe DO. Quantitative mapping of ventilation-perfusion ratios in lungs by 19F MR imaging of T1 of inert fluorinated gases. *Magn Reson Med* 59: 739-746, 2008.
Agusti AG, Roca J, Gea J, Wagner PD, Xaubet A, and Rodriguez-Roisin R. Mechanisms of gas-exchange impairment in idiopathic pulmonary fibrosis. *Am Rev Respir Dis* 143: 219-225, 1991.
Albert MS, Cates GD, Driehuys B, Happer W, Saam B, Springer CSJ, and Wishnia A. Biological magnetic resonance imaging using laser-polarized 129Xe. *Nature* 370: 199-201, 1994.
Almquist H, Jonson B, Palmer J, Valind S, and Wollmer P. Regional VA/Q ratios in man using 133Xe and single photon emission computed tomography (SPECT) corrected for attenuation. *Clin Physiol* 19: 475-481, 1999.
Altemeier WA, Robertson HT, and Glenny RW. Pulmonary gas-exchange analysis by using simultaneous deposition of aerosolized and injected microspheres. *J Appl Physiol* 85: 2344-2351, 1998.
Amis TC, Jones HA, and Hughes JM. Effect of posture on inter-regional distribution of pulmonary ventilation in man. *Respir Physiol* 56: 145-167, 1984.
Chen Q, Jakob PM, Griswold MA, Levin DL, Hatabu H, and Edelman RR. Oxygen enhanced MR ventilation imaging of the lung. *MAGMA* 7: 153-161, 1998.
Davidson MR. Further considerations in a theoretical description of gas-transport in lung airways. *Bull Math Biol* 43: 517-548, 1981.

Edelman RR, Hatabu H, Tadamura E, Li W, and Prasad PV. Noninvasive assessment of regional ventilation in the human lung using oxygen-enhanced magnetic resonance imaging. *Nat Med* 2: 1236-1239, 1996.
Elliott AR, Prisk GK, Guy HJ, and West JB. Lung volumes during sustained microgravity on Spacelab SLS-1. *J Appl Physiol* 77: 2005-2014, 1994.
Engel LA. Gas mixing within the acinus of the lung. *J Appl Physiol* 54: 609-618, 1983.
Glenny RW, and Robertson HT. Fractal properties of pulmonary blood flow: characterization of spatial heterogeneity. *J Appl Physiol* 69: 532-545, 1990.
Hatabu H, Alsop DC, Listerud J, Bonnet M, and Gefter WB. T2* and proton density measurement of normal human lung parenchyma using subillisecond echo time gradient echo magnetic resonance imaging. *Eur J Radiol* 29: 245-252, 1999.
Henderson AC, Prisk GK, Levin DL, Hopkins SR, and Buxton RB. Characterizing pulmonary blood flow distribution measured using arterial spin labeling. *NMR Biomed* 22: 1025-1035, 2009.
Hickam JB, Blair E, and Frayser R. An open-circuit helium method for measuring functional residual capacity and defective intrapulmonary gas mixing. *J Clin Invest* 33: 1277-1286, 1954.
Hopkins SR, Henderson AC, Levin DL, Yamada K, Arai TJ, Buxton RB, and Prisk GK. Vertical gradients in regional lung density and perfusion in the supine human lung: the Slinky effect. *J Appl Physiol* 103: 240-248, 2007.
Jakob PM, Wang T, Schultz G, Hebestreit H, Hebestreit A, and Hahn D. Assessment of human pulmonary function using oxygen-enhanced T(1) imaging in patients with cystic fibrosis. *Magn Reson Med* 51: 1009-1016, 2004.
Kaneko K, Milic-Emili J, Dolovich MB, Dawson A, and Bates DV. Regional distribution of ventilation and perfusion as a function of body position. *J Appl Physiol* 21: 767-777, 1966.
Kim, Tae Hoon, Authorized Officer, Korean Intellectual Property Office, International Search Report and Written Opinion, International Application No. PCT/US2011/063854, Jul. 27, 2012, 8 pages.
Levin DL, Buxton RB, Spiess jP, Arai T, Balouch J, and Hopkins SR. Effects of age on pulmonary perfusion heterogeneity measured by magnetic resonance imaging. *J Appl Physiol* 102: 2064-2070, 2007.
Lewis SM, Evans JW, and Jalowayski AA. Continuous distributions of specific ventilation recovered from inert-gas washout. *J Appl Physiol* 44: 416-423, 1978.
MacFall JR, Charles HC, Black RD, Middleton H, Swartz JC, Saam B, Driehuys B, Erickson C, Happer W, Cates GD, Johnson GA, and Ravin CE. Human lung air spaces: potential for MR imaging with hyperpolarized He-3. *Radiology* 200: 553-558, 1996.
Mai VM, Bankier AA, Prasad PV, Li W, Storey P, Edelman RR, and Chen Q. MR ventilation-perfusion imaging of human lung using oxygen-enhanced and arterial spin labeling techniques. *J Magn Reson Imaging* 14: 574-579, 2001.
Mai VM, Chen Q, Bankier AA, and Edelman RR. Multiple inversion recovery MR subtraction imaging of human ventilation from inhalation of room air and pure oxygen. *Magn Reson Med* 43: 913-916, 2000.
Mai VM, Tutton S, Prasad PV, Chen Q, Li W, Chen C, Liu B, Polzin j, Kurucay S, and Edelman RR. Computing oxygen-enhanced ventilation maps using correlation analysis. *Magn Reson Med* 49: 591-594, 2003.
Milic-Emili J, Henderson JA, Dolovich MB, Trop D, and Kaneko K. Regional distribution of inspired gas in the lung. *J Appl Physiol* 21: 749-759, 1966.
Milic-Emili j. Radioactive xenon in the evaluation of regional lung function. *Semin Nucl Med* 1: 246-262, 1971.
Musch G, Layfield JD, Harris RS, Vidal Melo MF, Winkler T, Callahan RJ, Fischman AJ, and Venegas JG. Topographical distribution of pulmonary perfusion and ventilation, assessed by PET in supine and prone humans. *J Appl Physiol* 93: 1841-1851, 2002.
Naish jH, Parker GJ, Beatty PC, Jackson A, Young SS, Waterton JC, and Taylor CJ. Improved quantitative dynamic regional oxygen-enhanced pulmonary imaging using image registration. *Magn Reson Med* 54: 464-469, 2005.

(56) References Cited

OTHER PUBLICATIONS

Ohno Y, and Hatabu H. Basics concepts and clinical applications of oxygen-enhanced MR imaging. *Eur J Radio* 164: 320-328, 2007.
Ohno Y, Hatabu H, Higashino T, Kawamitsu H, Watanabe H, Takenaka D, van Cauteren M, and Sugimura K. Centrically reordered inversion recovery half-Fourier single-shot turbo spin-echo sequence: improvement of the image quality of oxygen-enhanced MRI. *Eur J Radio* 152: 200-205, 2004.
Ohno Y, Hatabu H, Takenaka D, Adachi S, Van Cauteren M, and Sugimura K. Oxygen-Enhanced MR Ventilation Imaging of the Lung: Preliminary Clinical Experience in 25 Subjects. *Am J Roentgenol* 177: 185-194, 2001.
Ohno Y, Hatabu H, Takenaka D, Uematsu H, Ohbayashi C, Higashino T, Nogami M, Yoshimura M, Fujii M, and Sugimura K. Dynamic MR imaging: value of differentiating subtypes of peripheral small adenocarcinoma of the lung. *Eur J Radiol* 52: 144-150, 2004.
Paiva M. Gas transport in the human lung. *J Appl Physiol* 35: 401-410, 1973.
Prisk GK, Guy HJ, Elliott AR, Paiva M, and West JB. Ventilatory inhomogeneity determined from multiple-breath washouts during sustained microgravity on Spacelab SLS-1. *J Appl Physiol* 78: 597-607, 1995.
Prisk GK, Hammer J, and Newth CJ. Techniques for measurement of thoracoabdominal asynchrony. *Pediatr Pulmono* 134: 462-472, 2002.
SA, Rui Carlos et al., Vertical distribution of specific ventilation in normal supine humans measured by oxygen-enhanced proton MRI, J. App. Physiol 109: 1950-1959, 2010, pp. 1950-1959.
Silvennoinen MJ, Kettunen MI, and Kauppinen RA. Effects of hematocrit and oxygen saturation level on blood spin-lattice relaxation. *Magn Reson Med* 49: 568-571, 2003.
Theilmann RJ, Arai TJ, Samiee A, Dubowitz DJ, Hopkins SR, Buxton RB, and Prisk GK. Quantitative MRI measurement of lung density must account for the change in $T(2)(*)$ with lung inflation. *J Magn Reson Imaging* 30: 527-534, 2009.
Wagner PD, Laravuso RB, Uhl RR, and West JB. Continuous distributions of ventilation-perfusion ratios in normal subjects breathing air and 100 percent O2. *J Clin Invest* 54: 54-68, 1974.
Arai TJ et al. "Hypoxic pulmonary vasoconstriction does not contribute to pulmonary blood flow heterogeneity in normoxia in normal supine humans," J Appl Physiol 106: pp. 1057-1064, 2009.
Arnold JF et al', "Imaging lung function using rapid dynamic acquisition of T1-maps during oxygen enhancement," Magma 16: pp. 246-253, 2004.
Bolar DS et al. "Quantification of regional pulmonary blood flow using ASL-FAIRER," Magn Reson Med 55: pp. 1308-1317, 2006.

Briguori C. et al. "Gadolinium-based contrast agents and nephrotoxicity in patients undergoing coronary artery procedures," Catheter Cardiovasc Interv 67: pp. 175-180, 2006.
Burnham KJ et al, "Pulmonary perfusion heterogeneity is increased by sustained, heavy exercise in humans," J Appl Physiol 107: pp. 1559-1568, 2009.
Deninger AJ et al. "Assessment of a single-acquisition imaging sequence for oxygen-sensitive (3)He-MRI,". Magn Reson Med 47: pp. 105-114, 2002.
Deninger AJ et al. "Quantification of regional intrapulmonary oxygen partial pressure evolution during apnea by (3)He MRI," J Magn Reson 141: pp. 207-216, 1999.
Eberle B. et al. "Analysis of intrapulmonary O(2) concentration by MR imaging of inhaled hyperpolarized helium-3," J Appl Physiol 87: pp. 2043-2052, 1999.
Elmstahl B., "Gadolinium contrast media are more nephrotoxic than iodine media. The importance of osmolality in direct renal artery injections," Eur Radiol, 2006, 9 pages.
Fischer MC "Single-acquisition sequence for the measurement of oxygen partial pressure by hyperpolarized gas MRI," Magn Reson Med 52: pp. 766-773, 2004.
Henderson AC et al. "Steep Head-Down Tilt Has Persisting Effects on the Distribution of Pulmonary Blood Flow," J Appl Physiol, 2006, pp. 583-589.
Hlastala MP, and Robertson HT. Inert gas elimination characteristics of the normal and abnormal lung. J Appl Physiol 44: 258-266, 1978.
Hlastala MP. Multiple inert gas elimination technique. J Appl Physiol 56: 1-7, 1984.
Holverda S. et al. "Measuring Lung Water: Ex-Vivo Validation of Multi-Image Gradient Echo MRI," J Magn Reson Imaging: Jul. 2011, pp. 220-224.
Hopkins SR et al. "Lung perfusion measured using magnetic resonance imaging: New tools for physiological insights into the pulmonary circulation," J Magn Reson Imaging (in press): 2010, pp. 1287-1301.
Hopkins SR et al. "Pulmonary blood flow heterogeneity during hypoxia and high-altitude pulmonary edema," Am J Respir Crit Care Med 171, pp. 83-87, 2005.
Lopez AD et al. "Global and regional burden of disease and risk factors, 2001: systematic analysis of population health data," Lancet 367: pp. 1747-1757, 2006.
Loyd JE et al. "Heterogeneity of pathologic lesions in familial primary pulmonary hypertension," Am Rev Respir Dis 138: pp. 952-957, 1988.
Loyd JE et al. Familial primary pulmonary hypertension: clinical patterns. Am Rev Respir Dis 129: pp. 194-197, 1984.
Loyd JE. "Genetics and pulmonary hypertension," Chest 122: 284S-286S, 2002.

\* cited by examiner

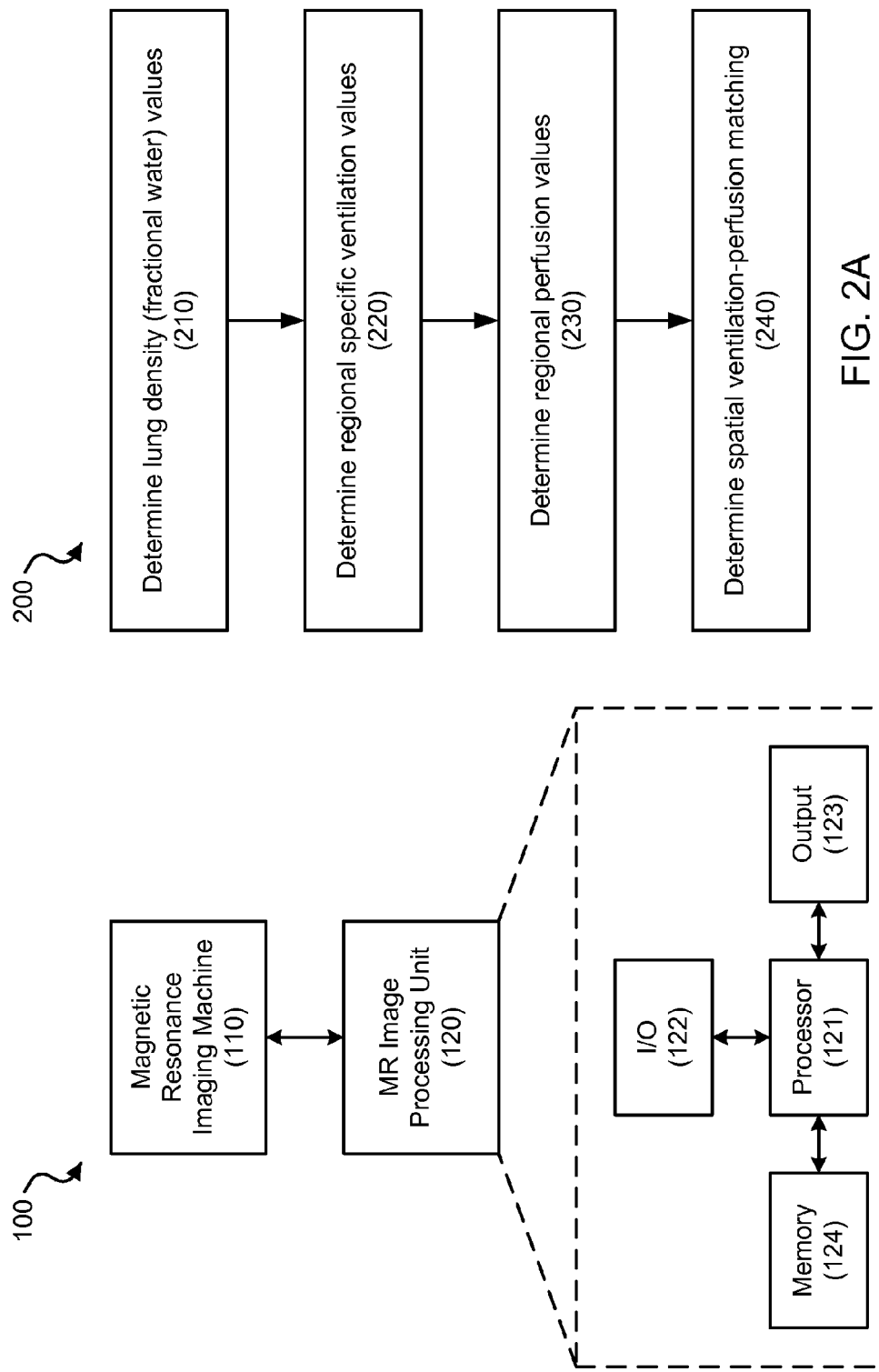

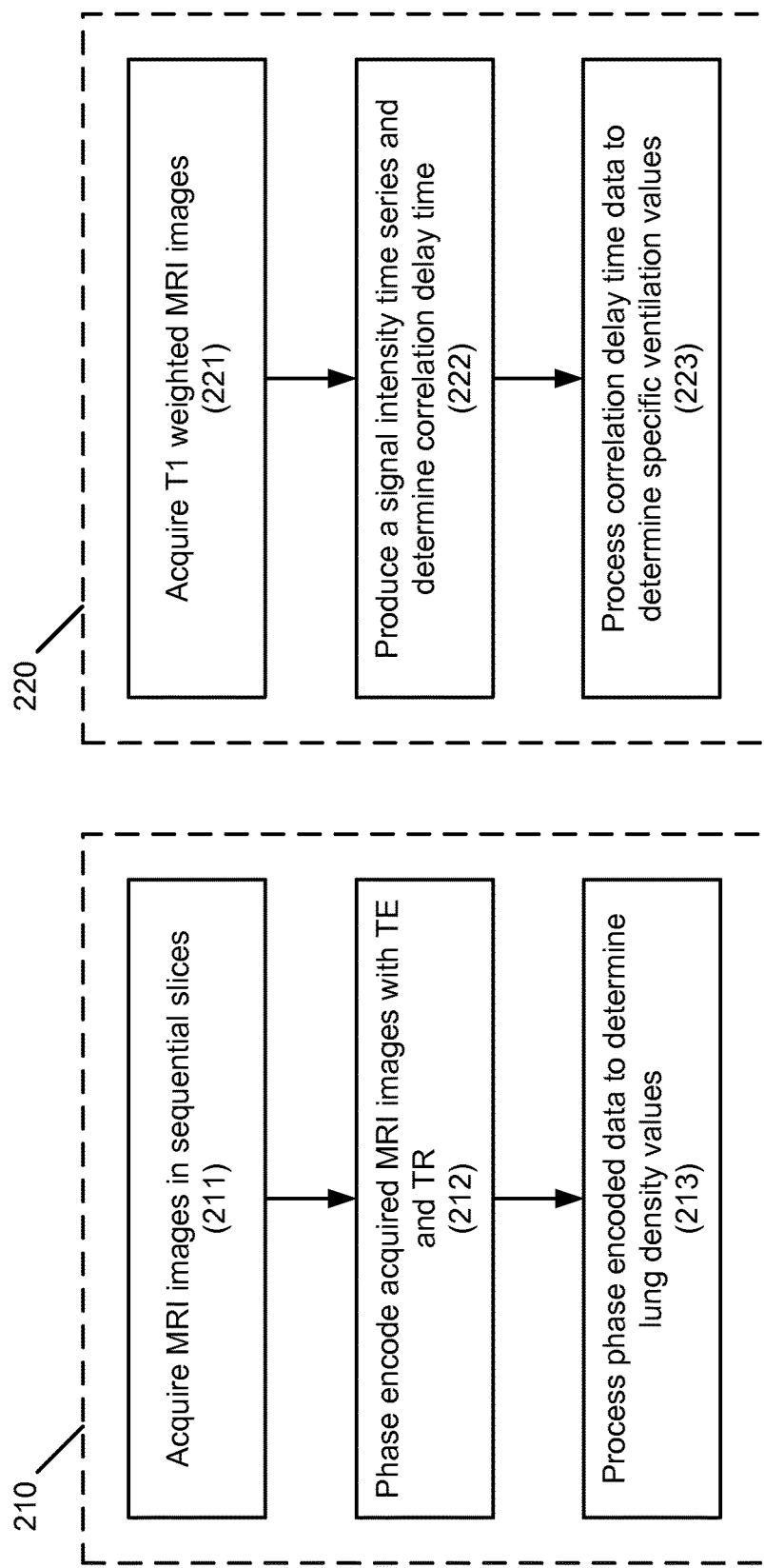

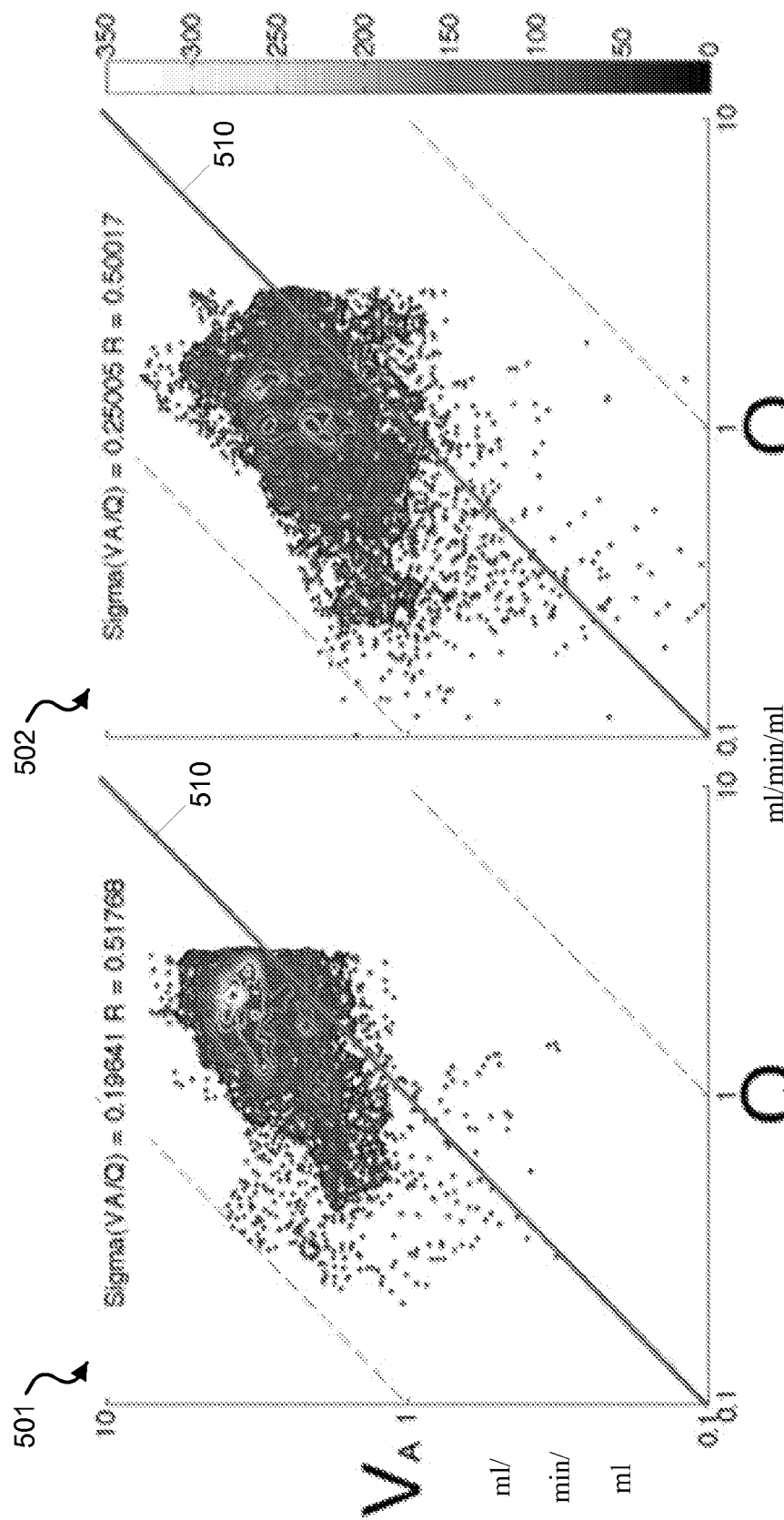

MAGNETIC RESONANCE IMAGING OF VENTILATION AND PERFUSION IN THE LUNG

CROSS-REFERENCE TO RELATED APPLICATION

This patent document claims priority of U.S. Provisional Patent Application No. 61/420,554, filed Dec. 7, 2010, entitled "IMAGING VENTILATION AND PERFUSION IN THE LUNG USING MRI". The entire content of the before-mentioned patent application is incorporated by reference as part of the disclosure of this application.

STATEMENT REGARDING FEDERALLY SPONSORED RESEARCH OR DEVELOPMENT

This invention was made with government support under grants EB005970, HL080203, and HL081171 awarded by the National Institutes of Health (NIH), along with a National Aeronautics and Space Administration (NASA) grant NCC9-58 #PF02103, awarded through the National Space Biomedical Research Institute (NSBRI). The government has certain rights in the invention.

BACKGROUND

This patent document relates to magnetic resonance image (MRI) technologies.

The lungs are primarily responsible for gas exchange, as well as a number of other functions. Ventilation of the lungs refers to the intake and removal of air in/out of the lungs, which involves the mixing of inspired gas (inhaled gas that is humidified and at body temperature) with alveolar gas for gas exchange of oxygen ($O_2$) and carbon dioxide ($CO_2$) in the alveoli of the lungs. Perfusion refers to the delivery of blood to capillary beds of a biological structure, e.g., alveoli in the lungs.

MRI is a medical imaging technique that applies a magnetic field and a pulse of radio frequency (RF) energy to produce an image used for imaging internal biological structures, e.g., the lungs. MRI is based on the property of nuclear magnetic resonance (NMR). NMR is a physical property in which the nuclei of atoms absorb and re-emit electromagnetic energy at a specific resonance frequency in the presence of a magnetic field. The absorption and reemission of energy can be dependent on the strength of the magnetic field and the magnetic property of the atoms (e.g., atoms whose nuclei possesses magnetic spin).

SUMMARY

Techniques, systems, and devices are disclosed for implementing a quantitative, non-injectable contrast MRI technique to measure spatial ventilation-perfusion matching.

In one aspect of the disclosed technology, a method using magnetic resonance imaging to characterize ventilation and perfusion in a lung includes acquiring a magnetic resonance (MR) image of the lung that includes MR data in a voxel of the MR image, which includes obtaining a breathing frequency parameter, determining a water density value, a specific ventilation value, and a perfusion value in at least one voxel of the MR image based on the MR data, which the water density value is used to determine an air content value, and determining a ventilation-perfusion ratio value that is the product of the specific ventilation value, the air content value, the inverse of the perfusion value, and the breathing frequency.

Various implementations of the above aspect can include one or more of the following features. The method can include the MR image being a 2D image. The method can include the MR image being a 3D image. The method can include determining the ventilation-perfusion ratio value voxel-by-voxel. The method can include acquiring the MR image using oxygen as an inhaled contrast agent. The method can further include determining an alveolar ventilation value that is the product of the specific ventilation value, the air content value, and the breathing frequency. The method can include producing a spatial distribution of ventilation, perfusion, and ventilation-perfusion using the ventilation-perfusion ratio value, the alveolar ventilation value, and the perfusion value. The method can include producing an image that shows the spatial distribution of ventilation, perfusion, and ventilation-perfusion for each voxel associated with the acquired MR image, and the spatial distribution of ventilation, perfusion, and ventilation-perfusion can be used as an indicator of a healthy or a diseased lung. The method can include determining ventilation-perfusion matching in the lung based on the ventilation-perfusion ratio value, and ventilation-perfusion matching can be used as an indicator of a healthy or a diseased lung.

In another aspect, an MRI system to characterize ventilation and perfusion in a lung includes an MRI machine and a processing unit. The MRI machine acquires an MR image of the lung. The processing unit is configured to command the magnetic resonance imaging machine to acquire the MR image that includes MR data in each voxel of the MR image, process the MR data to determine a water density value, a specific ventilation value, and a perfusion value in at least one voxel of the MR image, in which the water density value is used to determine an air content value, and determine a ventilation-perfusion ratio value that is the product of the specific ventilation value, the air content value, the inverse of the perfusion value, and a breathing frequency.

Various implementations of the above aspect can include one or more of the following features. The MRI system can use oxygen as an inhaled contrast agent to acquire the MR image of the lung. The processing unit can also be configured to determine an alveolar ventilation value that is the product of the specific ventilation value, the air content value, and the breathing frequency. The processing unit can also be configured to produce a spatial distribution of ventilation, perfusion, and ventilation-perfusion using the ventilation-perfusion ratio value, the alveolar ventilation value, and the perfusion value. The processing unit can also be configured to produce an image that shows the spatial distribution of ventilation, perfusion, and ventilation-perfusion for each voxel associated with the acquired MR image. The spatial distribution of ventilation, perfusion, and ventilation-perfusion can be used as an indicator of a healthy or a diseased lung. The processing unit can also be configured to determine ventilation-perfusion matching in the lung based on the ventilation-perfusion ratio value, and ventilation-perfusion matching can be used as an indicator of a healthy or a diseased lung.

In another aspect, a computer program product comprising a nonvolatile computer readable storage medium having instructions stored thereon includes code for acquiring an MR image of a lung that includes MR data in a voxel of the MR image, code for determining a water density value, a specific ventilation value, and a perfusion value in at least one voxel of the MR image based on the MR data, in which the water density value is used to determine an air content value, and code for determining a ventilation-perfusion ratio value that is the product of the specific ventilation value, the air content value, the inverse of the perfusion value, and a breathing frequency value.

Various implementations of the above aspect can include one or more of the following features. The code for acquiring the MRI image of the lung can include code using oxygen as an inhaled contrast agent. The nonvolatile computer readable storage medium can further include code for determining an alveolar ventilation value that is the product of the specific ventilation value, the air content value, and the breathing frequency. The code for determining the alveolar ventilation value can include code for producing a spatial distribution of ventilation, perfusion, and ventilation-perfusion using the ventilation-perfusion ratio value, the alveolar ventilation value, and the perfusion value. The code for determining the alveolar ventilation value can also include code for producing an image that shows the spatial distribution of ventilation, perfusion, and ventilation-perfusion for each voxel associated with the acquired MR image. The nonvolatile computer readable storage medium can further include code for using the spatial distribution of ventilation, perfusion, and ventilation-perfusion to indicate a healthy or a diseased lung. The nonvolatile computer readable storage medium can further include code for determining ventilation-perfusion matching in the lung based on the ventilation-perfusion ratio value. The code for determining ventilation-perfusion matching can further include code for using ventilation-perfusion matching to indicate a healthy or a diseased lung.

In another aspect, a method implementing a proton magnetic resonance imaging technique using oxygen as a contrast agent to quantify regional specific ventilation in a lung with magnetic resonance imaging includes acquiring T1 weighted images of a slice of a lung of a subject, in which the images are voluntarily respiratory gated by having the subject take a single breath following each image and then relax to functional residual capacity in time for a subsequent image, and detecting alterations in the images associated with a regional rise in oxygen concentration that reflect specific ventilation.

Various implementations of the above aspect can include one or more of the following features. The method can include acquiring T1 weighted images without a hyperpolarized gas. The T1 weighted images can be 2D images. The T1 weighted images can be 3D images. The acquiring T1 weighted images can use oxygen as an inhaled contrast agent. The method can further include producing an image that shows specific ventilation for each voxel associated with the acquired MR image. The method can include the specific ventilation being used as an indicator of a pulmonary pathological condition.

The disclosed technology can provide one or more of the following advantages. For example, the described methods, devices and systems can provide a fully quantitative non-injectable contrast agent proton MRI technique to measure spatial ventilation-perfusion ($V_A/Q$) matching and spatial distribution of ventilation and perfusion. The disclosed MRI techniques can be performed using an MRI system such as a standard 1.5 T clinical scanner, which can allow routine clinical imaging of patients. Implementation of the disclosed techniques can allow quantitative, noninvasive evaluation of important aspects of lung function. Implementation of the disclosed techniques can eliminate contrast injection and/or radiation hazard. This can be important for repeated evaluations, such as for research applications, and for screening patients with genetic predispositions to lung disease and with diseases such as collagen vascular diseases that have pulmonary manifestations.

BRIEF DESCRIPTION OF THE DRAWINGS

FIG. 1 shows an exemplary MRI-based ventilation-perfusion matching system.

FIGS. 2A-2D show diagrams of an exemplary MRI-based ventilation-perfusion method to characterize spatial $V_A/Q$ matching from MR images.

FIGS. 5A and 5B show exemplary plots of the spatial distribution of $V_A$, Q and $V_A/Q$.

Like reference symbols and designations in the various drawings indicate like elements.

DETAILED DESCRIPTION

Figure 2D:
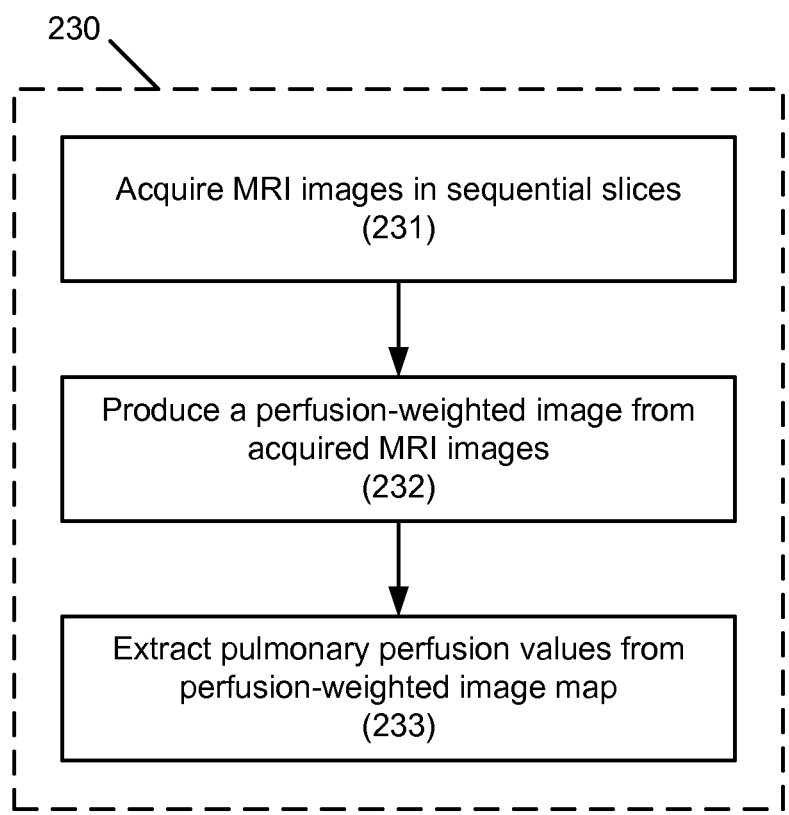

Techniques, devices and systems are described for implementing a quantitative, non-injectable contrast MRI technique to measure spatial ventilation-perfusion matching.

A primary function of the lung is gas exchange. The efficiency of gas exchange can be determined by matching of delivery of fresh gas by alveolar ventilation ($V_A$) to local perfusion (Q). $V_A/Q$ matching can be affected by passive mechanisms such as anatomical matching of the branching airway and blood vessel structures and by active mechanisms such as hypoxic pulmonary vasoconstriction. $V_A/Q$ matching can be used to characterize processes in which regions of the lung that receive fresh gas also receive deoxygenated capillary blood. Therefore, precise $V_A/Q$ matching within the millions of gas exchange units can be considered a fundamental mechanism to determine the efficiency of the gas exchange process, which can provide information on health and disease.

The measurement of ventilation-perfusion ($V_A/Q$) matching can be used as an indicator to distinguish between healthy or diseased lungs. For example, in normal or healthy lungs, the matching of ventilation to perfusion is relatively uniform, e.g., the mean and variance of $V_A/Q$ ratios are substantially identical for both ventilation and perfusion, and regions of high ventilation also receive high perfusion, with regions of low ventilation receiving low perfusion. For example, optimal $V_A/Q$ matching in the lung can be associated with tight, narrow, clusters of matched $V_A$ and Q or with broader, highly correlated distributions of $V_A$ and Q. In some cases, a broadening of the distributions with a maintained $V_A/Q$ matching can be considered as 'stressed' $V_A/Q$ matching—although matching is preserved, the lung may be at risk. For example, the lung can be considered overbuilt for many of the demands of daily life (except for the most strenuous exercise), and a region of loss of function may be compensated for by the remaining normal lung, which may delay diagnosis. Measurement of the separate spatial distribution of $V_A$ and Q as well as overall $V_A/Q$ can allow detection of this compensation. Therefore, it can be important to measure the spatial distribution of $V_A$ and Q as well as overall $V_A/Q$ matching.

$V_A/Q$ mismatch can be associated with lung disease, such as airway predominant diseases including asthma and diseases affecting the pulmonary circulation including pulmonary arterial hypertension (PAH). Lung disease is a leading cause of morbidity and mortality in the world. Various types of lung disease can be characterized by disruption of $V_A/Q$ matching, resulting in gas exchange inefficiency. For example, decreased $V_A/Q$ matching can be a hallmark of chronic obstructive pulmonary disease (COPD), with areas of both high $V_A/Q$ ratio (deadspace) and low $V_A/Q$ ratio described, and an overall decrease in $V_A/Q$ matching. Similarly, pulmonary hypertension, asthma, pulmonary edema, pulmonary fibrosis and adult respiratory distress syndrome can also be characterized by $V_A/Q$ mismatch.

For example, in patients with advanced lung disease, a diagnosis can be clinically observable, which can be confirmed with some diagnostic tools. Despite this, existing diagnostic tools such as spirometry can lack sensitivity and specificity, which may limit their utility for early diagnosis. For example, spirometry is not defined as abnormal until on average the patient has lost 20% of lung function. This can suggest that the normal compensatory mechanisms of the lung can prevent early detection of abnormalities, and can delay diagnosis and treatment. For example, a highly invasive and sparsely available diagnostic tool known as multiple inert gas elimination technique (MIGET) has been shown to be capable of identifying markedly abnormal $V_A/Q$ matching in patients with mild COPD (GOLD stage 1); while in the same patients, the changes in spirometry were shown to be mild and arterial oxygen and carbon dioxide levels were largely normal. This disruption of $V_A/Q$ matching in these patients can suggest that a quantitative technique to measure $V_A/Q$ matching can offer the ability to detect pre-clinical disease in COPD. Similarly, patients with pulmonary hypertension often do not present for medical care until the disease is well advanced. Pulmonary hypertensive patients also may have marked disruption of $V_A/Q$ matching at the time of diagnosis, suggesting that increased $V_A/Q$ mismatch can be an early feature of the disease. The disclosed technology can include a quantitative measurement of spatial $V_A/Q$ matching that can be used to enhance early disease identification and provide a noninvasive tool for monitoring disease progression and response to therapy, as well as quantitatively address research questions related to disease mechanisms.

The disclosed technology described in this patent document can be used to directly measure whole lung and spatial $V_A/Q$ matching in a manner that is fully quantitative, non-invasive, without radiation exposure, and clinically relevant (e.g., applicable and accessible to human patients). Implementation of the disclosed technology can provide the ability to measure spatial $V_A/Q$ matching and spatial distribution of ventilation and perfusion, which can, for example, be performed on a standard 1.5 T clinical scanner at the level of the gas exchange unit. Measured $V_A/Q$ matching and spatial distribution of $V_A$ and Q can be used to evaluate mechanisms of lung disease, injury, response to treatment and repair. For example, the disclosed techniques may be used in screening populations of patients at risk of developing lung disease and for monitoring response to treatment in those already afflicted. Routine clinical imaging of patients can be performed using the disclosed technology, e.g., allowing quantitative and noninvasive evaluations of the of lung function without concerns of radiation hazards and contrast injections.

In one aspect of the disclosed technology, three quantitative non-injectable contrast proton MRI techniques, that when implemented together, can allow regional ventilation, perfusion and spatial $V_A/Q$ matching to be directly measured, e.g., in the entire lung in humans. The measured values can be based on regions of the lungs. For example, MR images of the lung of a subject can be partitioned into three gravitational regions, corresponding to thirds of the lung based on equal vertical extent, e.g., a dependent region (region which is lowest with respect to the direction of the gravity vector); an intermediate region (region between dependent and non-dependent regions); and the non-dependent region (region which is highest with respect to the direction of the gravity vector). One technique of the disclosed technology can include a T2* multi-echo, fast gradient echo (mGRE) sequence for the rapid measurement of lung density (fractional water) in g (of water)/cm$^3$. Another technique of the disclosed technology can include a specific ventilation imaging (SVI) technique, which can use oxygen as a contrast agent for the measurement of regional specific ventilation, e.g., the dimensionless ratio of tidal volume (fresh gas) to functional residual capacity (residual gas at the end of a normal exhalation) of each lung element. Another technique of the disclosed technology can include an arterial spin labeling (ASL) technique, which can directly quantify regional pulmonary blood flow (perfusion) in units of mL (of blood)/min/cm$^3$. The disclosed MRI technology can apply appropriate scaling such that the measurements provided by the three exemplary techniques (e.g., mGRE, SVI, and ASL techniques) can be processed to provide quantitative spatial $V_A/Q$ matching and spatial distribution of $V_A$ and Q, e.g., on a voxel by voxel basis. For example, by combining the measured specific ventilation data with proton density measurements, alveolar ventilation ($V_A$) can be determined, such that when combined with perfusion measurements, can provide a fully quantitative measure of $V_A/Q$ used to determine $V_A/Q$ matching. For example, the disclosed MRI technology can measure T1 enhancement as a function of breath number to calculate an oxygen wash-in, and from that, be used to determine specific ventilation. Separate proton density measures can then be used to calculate $V_A$ from specific ventilation, and combined with separate measures of perfusion giving a fully quantitative measure of ventilation-perfusion matching.

FIG. 1 shows an exemplary MRI-based ventilation-perfusion matching system (100) for providing a quantitative, noninvasive measure of spatial $V_A/Q$ matching. FIG. 1 shows one aspect of the exemplary system (100) that can include a magnetic resonance imaging (MRI) machine (110), which can be controlled by a MR image processing unit (120).

The exemplary MRI machine (110) can be used in the system (100) to implement a MRI-based ventilation-perfusion matching characterization process under the control of the exemplary MR image processing unit (120). MRI machine (110) can include various types of MRI systems, which can perform at least one of a multitude of MRI scans that can include, but are not limited to, T1-weighted MRI scans, T2-weighted MRI scans, T2*-weighted MRI scans, spin (proton ($^1$H)) density weighted MRI scans, diffusion tensor (DT) and diffusion weighted imaging (DWI) MRI scans, T1ρ MRI scans, magnetization transfer (MT) MRI scans, real-time MRI, functional MRI (fMRI) and related techniques such as arterial spin labeling (ASL), among other MRI techniques.

The exemplary MR image processing unit (120) can include a processor (121) that can be in communication with an input/output (I/O) unit (122), an output unit (123), and a memory unit (124). MR image processing unit (120) can be implemented as one of various data processing systems, such as a personal computer (PC), laptop, tablet, and mobile communication device. To support various functions of MR image processing unit (120), the exemplary processor (121) can be included to interface with and control operations of other components of MR image processing unit (120), such as the exemplary I/O unit (122), the exemplary output unit (123), and the exemplary memory unit (124).

To support various functions of the MR image processing unit (120), memory unit (124) can store other information and data, such as instructions, software, values, images, and other data processed or referenced by processor (121). Various types of Random Access Memory (RAM) devices, Read Only Memory (ROM) devices, Flash Memory devices, and other suitable storage media can be used to implement storage functions of memory unit (124). The exemplary memory unit (124) can store MRI data and information, which can include subject MRI image data including spatial and spectral data. MRI machine system parameters, data processing parameters, and processed parameters and data that can be used in the implementation of a $V_A/Q$ matching characterization. Memory unit (124) can store data and information that can be used to implement a MRI-based $V_A/Q$ matching characterization process and that can be generated from a MRI-based $V_A/Q$ matching characterization algorithm and model.

To support various functions of the MR image processing unit (120), the exemplary I/O unit (122) can be connected to an external interface, source of data storage, or display device. Various types of wired or wireless interfaces compatible with typical data communication standards, such as Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), and parallel interfaces, can be used to implement I/O unit (122). I/O unit (122) can interface with an external interface, source of data storage, or display device to retrieve and transfer data and information that can be processed by the processor (121), stored in the memory unit (124), or exhibited on the output unit (123).

To support various functions of the MR image processing unit (120), the output unit (123) can be used to exhibit data implemented by the exemplary MR image processing unit (120). The output unit (123) can include various types of display, speaker, or printing interfaces to implement the exemplary output unit (123). For example, the output unit (123) can include cathode ray tube (CRT), light emitting diode (LED), or liquid crystal display (LCD) monitor or screen as a visual display to implement the output unit (123). In other examples, the output unit (123) can include toner, liquid inkjet, solid ink, dye sublimation, inkless (such as thermal or UV) printing apparatuses to implement the output unit (123); the output unit (123) can include various types of audio signal transducer apparatuses to implement the output unit (123). The output unit (123) can exhibit data and information, such as patient diagnostic data, MRI machine system information, partially processed MRI-based $V_A/Q$ matching characterization processing information, and completely processed MRI-based $V_A/Q$ matching characterization processing information. The output unit (123) can store data and information used to implement a MRI-based $V_A/Q$ matching characterization process and from an implemented MRI-based $V_A/Q$ matching characterization process.

FIG. 2A shows a process flow diagram that describes implementation of an exemplary MRI-based ventilation-perfusion method to measure spatial $V_A/Q$ matching from MR images, e.g., from the lung that can be used to assess lung function. Exemplary methods to characterize lung functionality using MRI techniques, such as water density measurement, specific ventilation measurement, alveolar ventilation measurement, perfusion measurement, ventilation-perfusion ratio measurement, and ventilation-perfusion matching, can be performed on systems and devices, such as the exemplary system (100) illustrated in FIG. 1. For example, FIG. 2A shows an exemplary method (200) to characterize spatial $V_A/Q$ matching from MR image(s) that includes a process (210) to determine lung density (water fraction) values from an MR image of a lung in a desired target, a process (220) to determine regional specific ventilation values from an MR image of the lung in the desired target, a process (230) to determine regional pulmonary perfusion values in an MR image of the lung in the desired target, and a process (240) to determine spatial ventilation-perfusion matching in the lung of the desired target, e.g., by combining and processing the resultant values process (210), process (220), and process (230). Process (240) can also include characterizing the spatial distribution of ventilation and perfusion. Exemplary method (200) can implement exemplary processes (210), (220), and (230) in the order shown in FIG. 2A, or in any other order not shown in the exemplary figure.

Process (210) can include performing MR imaging on an MRI machine, e.g., MRI machine (110), using 2D or 3D multiple gradient-recalled echo (mGRE) sequence and/or other types of sequence. Process (210) can characterize regional lung water density (water fraction) by using an exemplary mGRE sequence technique to provide rapid acquisition of lung proton density data on a voxel by voxel basis. For example, lung proton density data can be acquired at rates ~8 seconds/slice. The described mGRE sequence technique can provide a measurement of regional lung water compensated for potential differences in T2*.

The exemplary mGRE sequence technique can include a pulse sequence of a small flip angle slice selective excitation followed immediately by the collection of a single full line of Fourier data. The sequence can acquire data at 2 echo times, and the proton density of the lung can be determined by back extrapolating the signal to an echo time (TE), e.g., TE=0, by fitting data points to a single exponential.

FIG. 2B shows a diagram of an exemplary 2D acquisition sequence to determine lung density (water fraction) values in process (210). In this example, process (210) can include process (211) that includes collecting 2D MRI images in sequential slices across the lung field, e.g., at 2 echo times.

Implementation of the exemplary 2D acquisition sequence on a slice with a thickness of substantially 15 mm can be covered over the entire lung in approximately 9 minutes (e.g., ~18 slices*10 sec per scan, 20 sec recovery). The exemplary 2D acquisition sequence to acquire MRI images in process (211) can include a single RF pulse followed by a single full line of Fourier data. It is noted that acquisition time is limited by breath-hold time (e.g., less than 12 seconds in some patient populations. Process (212) includes phase encoding the acquired image(s) at a fixed echo time (TE) and repetition time (TR) until k-space is filled for a single image. The sequence can then repeat by filling k-space acquired at a second echo time while keeping TR constant. Process (213) includes processing the phase encoded data, e.g., by fitting the data points to a single exponential decay function, to determine lung water density, as well as T2*. The exemplary mGRE sequence technique exemplified in FIG. 2B can be adapted from a 2D acquisition sequence to a 3D acquisition sequence. For example, an exemplary 3D acquisition sequence can be implemented in which one 3D image is acquired at each echo time (e.g., two 3D volumes), shortening acquisition time. For example, a single lung volume may be acquired in 6 seconds with an isotropic resolution of 8 mm³ with the following sequence parameters: echo time=0.7 ms and 1.2 ms, field of view=30 cm (A/P)×48 cm (R/L)×48 cm (S/I), repetition time=2.5 ms, flip angle=5°, matrix acquisition=40 (A/P)×64(R/L)×64 (S/I), and can increase in signal-to-noise ratio (SNR).

Process (220) can include performing proton MR imaging on an MRI machine, e.g., MRI machine (110). Process (220) can characterize specific ventilation (SV) and regional ventilation by using an exemplary specific ventilation imaging (SVI) technique. Specific ventilation (SV) is a measure of regional ventilation that can be determined by the ratio of fresh gas entering a lung region divided by its end-expiratory volume. Specific ventilation (SV) can be defined as the ratio of the volume of fresh gas ($\Delta V$) moving into a region of the lung to the end-expiratory volume ($V_0$) of that region, $SV=\Delta V/V_0$.

The exemplary SVI technique can be implemented in a single or multiple lung slice enabling two dimensional (2D) and three dimensional (3D) SV characterizations. The exemplary SVI technique can use 100% oxygen as a contrast agent. The SVI technique can include oxygen delivery to and dissolution in lung tissue, which can shorten the longitudinal relaxation time ($T_1$), increasing the local MRI signal. For example, $T_1$-weighted images can be acquired while a subject breathes air and then 100% $O_2$ in an alternating sequence. Since the amount of regional dissolved oxygen can be associated with the amount of oxygen locally available (e.g., determined by ventilation), the oxygen wash-in time for individual voxels can be determined. Voxels that have a high specific ventilation can reach the new equilibrium faster than units that are less ventilated. A quantitative measure of the specific ventilation (e.g., local tidal volume/ functional residual capacity (FRC)) of that portion of the lung can be determined, for example, considering the time delay between the onset of the stimulus (breathing 100% oxygen) and the response for a particular voxel.

FIG. 2C shows a diagram of an exemplary MRI imaging technique to determine to regional specific ventilation values in process (220). In this example, process (220) can include process (221) that includes acquiring 2D $T_1$ weighted MRI images, e.g., using an inversion recovery single shot fast spin echo sequence with images being acquired with a half Fourier acquisition. The exemplary process (221) can include using an inversion time of 1000 msec. Process (222) includes producing a signal intensity time series of the acquired MRI images and determining the correlation delay time using a shifted cross correlation between the inspired fractional oxygen concentration and the acquired signal intensity time series. Process (223) includes processing the correlation delay time to determine specific ventilation values, e.g., regional specific ventilation values, as described in further detail later in this patent document. Process (223) can also include producing a plot or map of the specific ventilation values. The exemplary SVI technique is not limited to 2D MRI acquisitions. The exemplary technique exemplified in FIG. 2C can be adapted from a 2D MRI technique to a 3D MRI technique.

Exemplary techniques to implement 3D ventilation imaging can be accomplished in a reasonable acquisition time, e.g., by co-registering with the proton density images, specific ventilation can be converted to $V_A$ as previously described. The exemplary SVI technique can map the change in signal intensity due to the local change in oxygen concentration effect on $T_1$. This contrast change can be enhanced by adding a global inversion recovery pulse prior to acquisition. As a result, 3D sampling techniques can be implemented to acquire the entire lung field. For example, one approach includes improving the acquisition speed (short $T_2$ in the lung) by a single-shot GRASE acquisition which can allow multiple 2D images to be acquired following an inversion pulse. Another approach includes implementing highly constrained back-projection for time-resolved MRI (HYPR) or vastly under-sampled isotropic projection reconstruction (VIPR) to significantly reduce the acquisition time and the echo time, thereby improving the overall SNR while allowing full 3D acquisition of the lung.

Process (230) can include performing MR imaging on an MRI machine, e.g., MRI machine (110), using 2D or 3D calibrated arterial spin labeling (ASL) technique and/or other technique. Process (230) can characterize the distribution of pulmonary perfusion by using the exemplary ASL technique to provide analysis of how the normal distribution of perfusion can be disrupted by a variety of insults, such as hypoxia, exercise and interstitial pulmonary edema. The described ASL technique can be respiratory and cardiac gated and fully quantitative.

The exemplary ASL technique can be used to quantify pulmonary perfusion using a 2D arterial spin labeling—flow-sensitive alternating inversion recovery with an extra radio frequency pulse (ASL-FAIRER) sequence with a half-Fourier acquisition single-shot turbo spin-echo (HASTE) imaging scheme. For example, two ECG-gated images (to collect data from a complete systolic ejection period) of each of the selected slices can be taken (e.g., 4 to 6 seconds apart, depending on heart rate) during two successive apneas with the glottis open at the desired lung volume. The images can be preceded by tagging pulses that invert the magnetization of arterial blood outside the imaging plane in one case, and leave it undisturbed in the other. Pairs of images so obtained can be subtracted, leaving an image of pulmonary blood flow delivered during one cardiac cycle. The orientation of the imaged slices of lung can be varied as desired. One example includes the sagittal plane, and voxel sizes of approximately 1.6×1.6×15 mm (~36 mm³ or 0.04 cm³) can be visualized.

FIG. 2D shows a diagram of an exemplary MRI imaging technique to determine to regional perfusion values in process (230). In this example, process (230) can include process (231) that includes acquiring 2D MRI images, e.g., an ASL-FAIRER sequence with a HASTE imaging scheme in sequential slices. In FAIRER, an image is acquired by applying a spatially selective inversion pulse, followed by a saturation pulse, followed by dephasing gradients. An adequate delay can allow relaxed spins to enter from adjacent tissue and displace saturated spins. Imaging can begin after this delay. The imaging slice and inversion slice can be centered on the same plane to overlap. Complete inversion of the spins in the image plane can include making the width of the selective inversion pulse substantially wider than the image slice thickness. This can be repeated with the spatially selective inversion pulse replaced by a nonspatially-selective inversion pulse. This can, for example, invert all of the spins in the volume covered by the RF body coil. The same delay can allow inverted spins to enter the imaging plane. Process (232) can include producing a perfusion-weighted image map, e.g., by subtraction of the spatially-selective tagged image from the non-spatially-selective tagged image. It is noted that the addition of the extra RF pulse and dephasing gradients, for example, can prevent the zeroing of signal intensity in certain voxels upon subtraction. Process (233) can determine regional pulmonary perfusion values by extracting perfusion data from the produced perfusion-weighted image map.

An exemplary 3D ASL acquisition technique to acquire perfusion data in the lung can include collecting each tag/control pair in sequential slices such that the entire dataset encompasses the entire lung. Data for each sagittal slice can be collected during sequential breath holds at functional residual capacity moving from the medial chest adjacent to the mediastinum to the lateral chest wall. A complete 3D lung dataset may only take ~3 minutes to acquire with respiratory gating between repetition times, e.g., ~5 sec. This whole sequence can be repeated for signal averaging or to ensure image quality. A more complex, but more efficient, approach for 3D ASL data acquisition can include interleaving the ASL with the SVI acquisition, shortening the combined acquisition time for the two images.

Figures 3A, 3B, 3C:
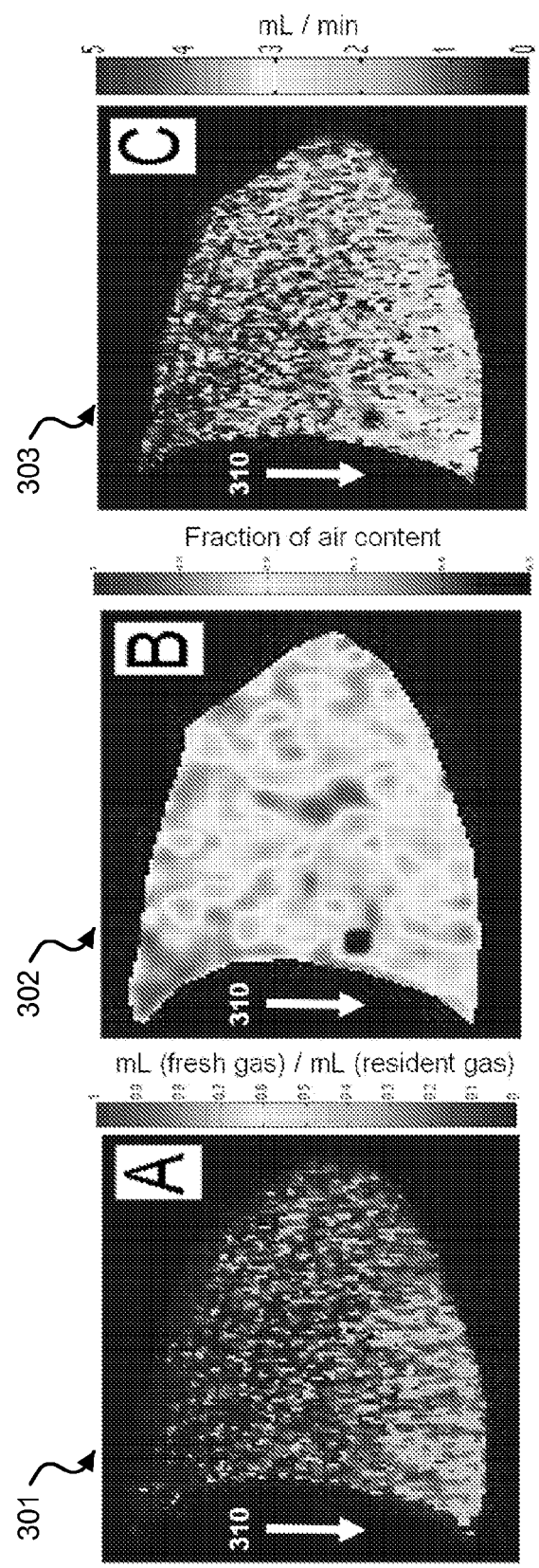
FIG. 3A shows an exemplary quantitative image of regional specific ventilation.
FIG. 3B shows an exemplary quantitative image of regional air content.
FIG. 3C shows an exemplary quantitative map of regional alveolar ventilation.

FIGS. 3A, 3B and 3C show exemplary quantitative images of regional specific ventilation (FIG. 3A) and regional air content (FIG. 3B) to produce a map of regional alveolar ventilation (FIG. 3C) in a single sagittal slice from the right lung of an exemplary human subject in the supine position. FIG. 3A shows quantitative image (301) that exemplifies regional specific ventilation in the exemplary slice by implementing process (220). FIG. 3B shows quantitative image (302) that exemplifies regional air content in the exemplary slice by implementing process (210). FIG. 3C shows quantitative image (303) that exemplifies regional alveolar ventilation ($V_A$) determined on a voxel by voxel basis in the exemplary slice by implementing process (240). The exemplary color scale represents regional alveolar ventilation in $L \cdot min^{-1}$. The exemplary arrow (310) in FIGS. 3A, 3B, and 3C indicates the gravitational vector. As seen in FIGS. 3A and 3C, the exemplary quantitative image values of both specific ventilation image (301) and regional ventilation image (303) are greater in the gravitationally dependent region of the lung. This result may indicate, for example, that the nondependent region of the lung is already stretched and relatively poorly ventilated.

Figures 4A, 4B:
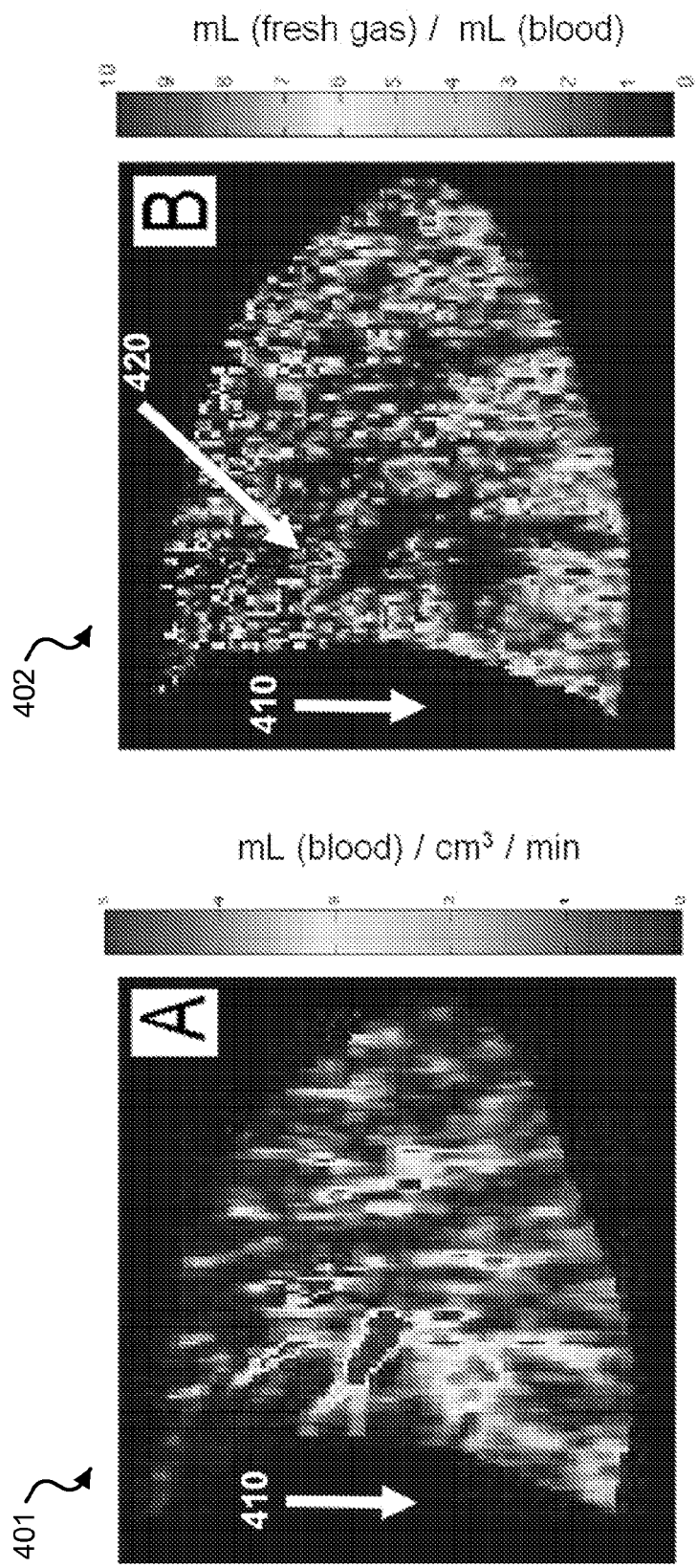
FIG. 4A shows an exemplary quantitative image of perfusion.
FIG. 4B shows an exemplary quantitative measure of regional ventilation-perfusion ratio.

FIGS. 4A and 4B show exemplary quantitative images of ASL measure of perfusion (FIG. 4A), which when combined with the measure of alveolar ventilation (303) can provide regional $V_A/Q$ ratio (FIG. 4B). The exemplary data shown in FIGS. 4A and 4B were analyzed from the exemplary sagittal slice of the subject as shown in FIGS. 3A-3C. FIG. 4A shows quantitative image (401) that exemplifies ASL measured perfusion data in the exemplary slice by implementing process (230). The exemplary arrow (410) indicates the gravitational vector.

FIG. 4B shows quantitative image (402) that exemplifies the regional ventilation-perfusion ratio in the exemplary slice by implementing process (240). In this exemplary implementation, the sagittal plane was chosen to demonstrate the well-known gravitational gradients in ventilation, perfusion and $V_A/Q$ ratio. In the example shown in FIG. 4B, the regions of higher $V_A/Q$ ratio are seen in the nondependent region of the lung. In the example, regions consistent with large vessels can be mapped as regions of shunt $V_A/Q$ (e.g. $V_A/Q$ ratio=0), as shown by arrow (420). The exemplary arrow (410) indicates the gravitational vector.

Process (240) can be used to determine spatial $V_A/Q$ matching and spatial distribution of $V_A$ and Q by implementation of an exemplary MRI-based $V_A/Q$ matching technique described herein. Specific ventilation can be measured in process (220), e.g., having units of mL (fresh gas)/mL (resident gas). Fractional lung density for any voxel can be measured in process (210), e.g., having units of mL (water)/cm³. In this context, both blood and other intra/extra-cellular water can be considered as water. For example, a voxel in the lung can include a mixture of water (fractional density 1) and air (fractional density 0). Thus, the value of [1−density] can be a direct measure of the air content of a voxel, which can be measured in units of mL (resident gas)/cm³, e.g., within a small error resulting from any tissue not producing an MRI signal.

The exemplary MRI-based $V_A/Q$ matching technique of process (240) uses the combination of specific ventilation (e.g., measured using the SVI technique in process (220)) and density (e.g., measured at FRC using the mGRE sequence technique in process (210)) on a voxel by voxel basis to provide a measure of fresh gas input to that voxel, in units of [mL (fresh gas)/mL (resident gas)]·[mL (resident gas)/cm³], e.g., mL (fresh gas)/cm³. For example, quantitative data from an acquired SV image (e.g., image (301)) can be multiplied by the breathing frequency ($f_B$) in units of min⁻¹, which can be imposed by the repetition time used in the SVI acquisition. The resultant value can be multiplied by the value of [1−density](e.g., quantitative data of air content) to provide a fully quantitative measure of alveolar ventilation ($V_A$), in units of mL (fresh gas)/cm³/min. $V_A$ can be determined for each voxel, which is represented in Eq. (1):

$$V_A = SVI \times (1-density) \times f_B \qquad (1)$$

where SVI represents quantitative data from an acquired SV image; (1−density) represents quantitative data of air content; and $f_B$ represents the breathing frequency.

For each voxel, a $V_A/Q$ ratio can be calculated by dividing the resultant $V_A$ image data (e.g., image (303)) by the quantitative value of perfusion in a voxel from an image (e.g., image (401)), e.g., from quantitative perfusion data measured using the ASL technique in process (230). $V_A/Q$ can be determined for each voxel, which is represented in Eq. (2):

$$V_A/Q = [SVI \times (1-density)/ASL] \times f_B \qquad (2)$$

where $V_A/Q$ represents a quantitative ratio of alveolar ventilation to perfusion and ASL represents quantitative perfusion data. From Eq. (2), $V_A/Q$ is represented in units of [mL (fresh gas)]/[mL (blood)].

Process (240) can further include a process to evaluate spatial distribution of $V_A$, Q and $V_A/Q$ ratios, the relationship of $\sigma(V_A/Q)$, the standard deviation (SD) of $V_A/Q$ ratios in logarithmic space, and $\sigma(V_A)$ and $\sigma(Q)$, the SD of the individual ventilation and perfusion distributions (e.g., in 2D) logarithmic space. For example, after calculating the voxel by voxel $V_A/Q$ ratio, some 5000-7000 points may be left, which can then be probed in a variety of ways. For example, plots of regional $V_A$ versus Q can be generated and the histograms of the individual distributions ($V_A$, Q, and $V_A/Q$) can be quantified. The correlation (r) between regional $V_A/Q$ and $V_A$ and Q can be calculated. The variance in the $V_A/Q$ heterogeneity can be related to the variance in $V_A$ and Q as described by Eq. (3) and Eq. (4) in logarithmic form:

$$\sigma(V_A/Q)^2 = \sigma(V_A)^2 + \sigma(Q)^2 - 2 \cdot r \cdot \sigma(V_A) \sigma(Q) \quad (3)$$

$$\sigma^2 \log(V_A/Q) = \sigma^2 \log V_A + \sigma^2 \log Q - 2 \cdot r \cdot \sigma \log V_A \cdot \sigma \log Q \quad (4)$$

where r is the correlation coefficient between $V_A$ and Q. Eqs. (3) and (4) show that different sets of $\sigma(V_A)$, $\sigma(Q)$, and r can produce substantially identical $\sigma(V_A/Q)$.

FIGS. 5A and 5B show two exemplary plots of the spatial distribution of $V_A$, Q and $V_A/Q$ for two healthy normal subjects. Plot (501) shown in FIG. 5A features spatial distribution of $V_A$, Q and $V_A/Q$ of one normal healthy subject. Plot (502) shown in FIG. 5B features spatial distribution of $V_A$, Q and $V_A/Q$ of the other normal healthy subject. The diagonal red line (510) represents a $V_A/Q$ ratio of 1. Voxels above line (510) have a $V_A/Q$ ratio above 1 (e.g., 'higher' $V_A/Q$ ratio). Voxel points below line (510) have a 'lower' $V_A/Q$ ratio. Plot (501) and plot (502) exhibit the overall $V_A/Q$ distribution slightly above 1, in which the majority of points range between a $V_A/Q$ ratio of 0.5 and 3. The range of $V_A/Q$ ratios can be considered important because it can be shown that this is the range of $V_A/Q$ ratios consistent with normal blood oxygenation and thus representing optimal $V_A/Q$ matching.

The exemplary method (200) can be implemented using system (100) or other MRI systems. In one example implementing the disclosed technology, MRI data can be collected from the exemplary subjects using a 1.5 Tesla Signa HDx TwinSpeed MRI system (e.g., General Electric Medical Systems, Milwaukee, Wis., USA). MR images can be taken from, for example, a single sagittal slice of the lung. A subject can be placed supine in the MRI scanner wearing a face mask (Hans Rudolph, Kans., USA), equipped with a non-rebreathing T-valve. The inspiratory port of the T-valve can be connected to a remote controlled valve allowing the operator to change from room air to gas contained in a large gas-tight bag filled from a gas cylinder in the control room. The inspiratory paths can be matched in airflow resistance to avoid any alteration in FRC when switching between them. The outlet of the T-valve can be connected to a long (e.g., 6 m), low resistance expiratory line, e.g., leading out of the scanner room, where expired tidal volume can be measured (e.g., using a ParvoMedics Metabolic Measurement System, (Sandy, Utah, USA)). Reference phantoms can be placed on the anterior chest wall so as to be within the field of view of the scans, permitting absolute quantification of blood flow and lung density. The subject can lie on the posterior element of an 8-channel cardiac coil, and the anterior elements are placed directly on the chest wall.

The exemplary MRI $V_A/Q$ matching technique can be implemented in 2D and 3D. 3D implementations of the disclosed technology may include additional considerations, e.g., accurate image registration at a sub-voxel resolution. Other considerations that can exist in 3D implementations can include effects on image registration from motion and tissue deformation as lung volume at FRC has small variations in subjects. Additionally, large blood vessels may represent shunt $V_A/Q$ ratios (e.g., an absence of ventilation that maps to a $V_A/Q$ ratio of zero) if a voxel represents an imaged space entirely filled with blood. However, since these large vessels are conduits, this does not represent a true shunt, which is an important contribution to pulmonary gas exchange abnormalities. The disclosed MRI $V_A/Q$ matching technique can include mechanisms to eliminate the contribution of large vessels from the image to accurately quantify true shunt. For large airways, these can be mapped as deadspace (regions that are ventilated but not perfused). Also, 3D implementations can involve longer data acquisition times than 2D, for example.

An important advantage of the disclosed techniques is that there is no "dose" associated with performing measurements, as there is no radiation or contrast injection to a target subject. Thus, the disclosed technology can allow repeated measurements to be performed on a subject under multiple conditions. For example, this can further benefit biomedical and physiological research design because each subject can act as their own control.

In another aspect of the disclosed technology, specific ventilation can be measured using proton MRI by using $O_2$ as a contrast agent. Exemplary implementations of disclosed techniques of this aspect can demonstrate a mapped distribution of specific ventilation in the lung, e.g., including the lung's gravitationally dependent gradient. Disclosed are exemplary devices, systems, and methods to quantify specific ventilation (SV).

Specific ventilation is a dimensionless quantity that provides a measure of how efficiently a given lung region is ventilated. For example, regional specific ventilation can be an important metric from a physiological standpoint, as well as also for clinical diagnosis and assessment of different pulmonary pathological conditions, e.g., asthma, emphysema, cystic fibrosis and lung cancer.

Oxygen is weakly paramagnetic, and when in solution in lung tissues can produce a measurable decrease in the longitudinal relaxation time T1 of tissues, increasing the signal intensity of an appropriately timed inversion recovery proton MR image. An exemplary technique can include using proton MRI technique in which inhaled oxygen ($O_2$) can be used as a contrast agent to verify the presence or absence of ventilation. Additionally, the disclosed technology can obtain an $O_2$-enhanced MRI signal that contains more information than just the presence or absence of ventilation. For example, the change in $O_2$ concentration in lung tissues (determining the local change in T1) depends on the rate of change of the $O_2$ alveolar concentration, which is a function of the regional specific ventilation. Thus, measurement of the regional rate of change of the MRI signal can allow the quantification of specific ventilation: Following a change in inspired fractional oxygen content ($F_1O_2$), units that have higher specific ventilation reach the new equilibrium faster than units that have a lower specific ventilation. Thus, the rapidity of the change in the MRI signal in a particular voxel or region following a change in inspired $F_1O_2$ is a quantitative measure of the specific ventilation of that portion of the lung.

Figure 6:
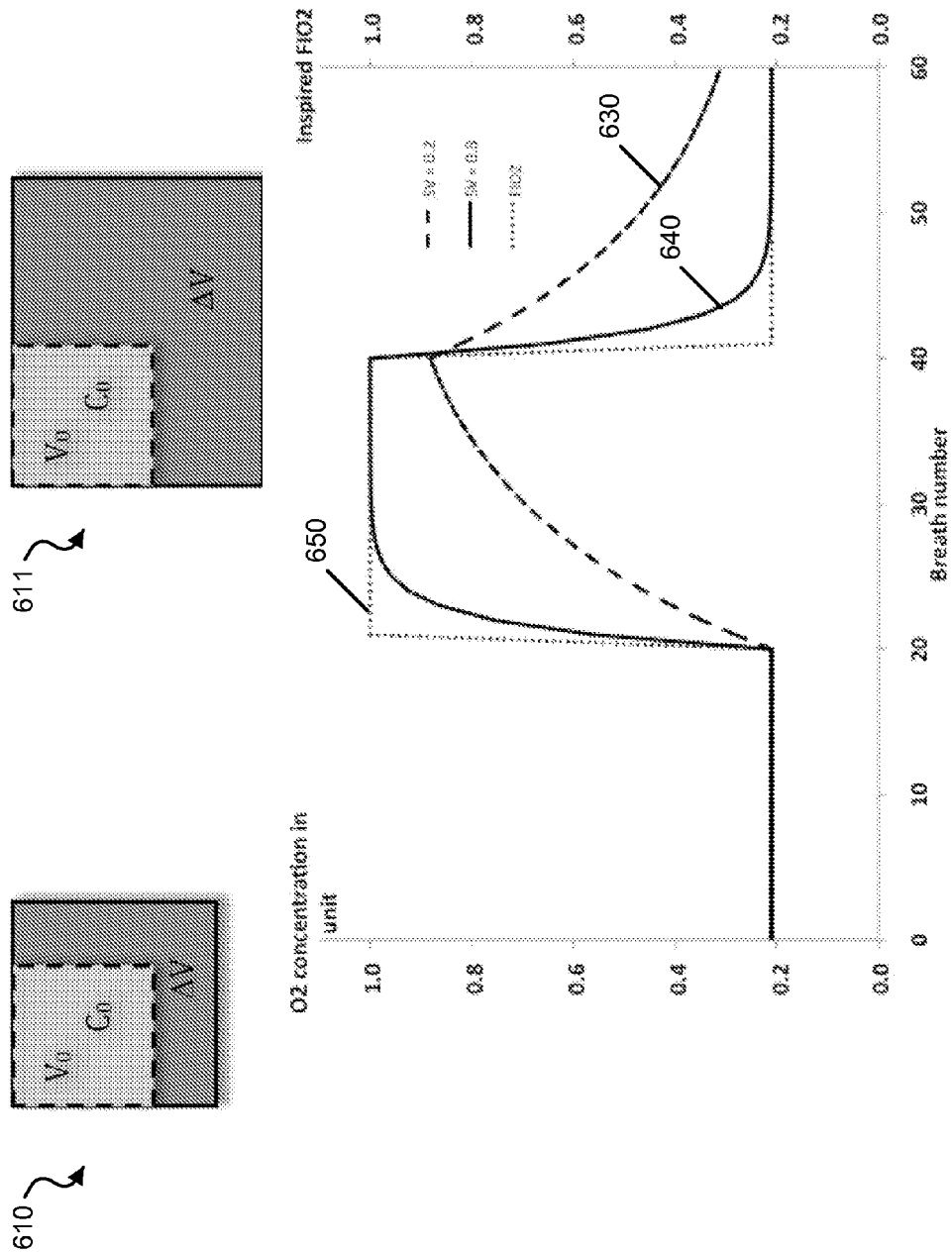
FIG. 6 shows an exemplary plot of specific ventilation of a lung unit.

In one example, following a sudden change in inspired fraction of $O_2$ ($F_1O_2$), the rate of change of the alveolar $O_2$ concentration is a function of the local specific ventilation, e.g., lung units with higher specific ventilation reach a new equilibrium faster than units with lower specific ventilation. The time it takes to reach a new equilibrium is a measure of the local specific ventilation. This time can be reflected in the MR images. For a series of inversion recovery images acquired with appropriate scanning parameters, the signal intensity change observed following a change in inspired gas can be determined by the change in relaxation time T1, e.g., a change driven by the local amount of oxygen in solution, which is a function of the local $O_2$ partial pressure. The time course of the regional MR signal intensity resulting from a change in inspired $O_2$-concentration can therefore reflect local specific ventilation. For example, the rapidity of the increase in the MRI signal intensity following the onset of $O_2$ inhalation is directly related to specific ventilation (as shown in FIG. 6, discussed later).

Exemplary Lung Unit Model and Simulated Data

An exemplary model of a lung unit is disclosed that can be used to translate the MRI signal rise time into a quantification of specific ventilation. The exemplary model of a lung unit corresponds to the voxel size measured with the MRI. The variable of interest in the exemplary model is the rate of equilibration (e.g., the rise time). For example, dead space, water vapor and end tidal partial pressure of $CO_2$ ($PCO_2$), factors that change the steady state equilibrium partial pressure of $O_2$ ($P_AO_2$), but remain largely constant during, can be ignored in many instances, as described herein. The exemplary lung unit model describes the temporal behavior of the $O_2$ concentration from the air breathing equilibrium value to the new 100% $O_2$ steady state.

Different ventilation-perfusion ($V_A/Q$) ratios can result in different steady state oxygen concentrations for both inspired air (e.g., ~range 50-100 mmHg, for $V_A/Q$ ratios between 0.001 and 10) and 100% inspired $O_2$ (e.g., ~550 to 600 mmHg, for the same range of $V_A/Q$ ratios). These exemplary steady state equilibrium conditions can provide adequate (and essentially similar) contrast for all reasonable $V_A/Q$ ratios. Further, the exemplary lung unit model is independent of the equilibrium or steady state conditions, e.g., it can be based on the rate of equilibration. For example, two lung units presenting identical $V_A/Q$ ratios and different specific ventilations are still distinguishable from each other by the different rate of equilibration, with the one presenting a higher SV having a faster turn-over, and thus equilibrating faster.

For the exemplary lung unit model, assumptions can be applied. For example, it can be assumed that a voxel dimension (1.6×1.6 mm in the imaging plane, for a 15 mm thick slice, volume ~40 mm$^3$) is small enough such that concentrations inside the unit at end expiration can be considered uniform, and therefore each voxel can be treated as a single ventilatory unit. Also, it can be assumed that the time interval between two consecutive acquired images (>5 sec) is long enough so that equilibrium between oxygen in the gas-phase and in solution in blood and tissues is attained by end expiration. Using either continuous (trumpet model) or discrete (asymmetrical branch point) models of the acinus, these exemplary approaches have shown that at the scale of existing resolution, oxygen concentration can be constant within a single respiratory pathway. Exemplary simulations in asymmetrical branch point models suggest differences in $O_2$ concentration can persist among parallel respiratory units, yet within each unit the $O_2$ concentration gradient can be essentially abolished, consistent with the exemplary assumption.

In the exemplary simulation, subjects can self gate their breathing to the 5 s interval between consecutive image acquisitions. Oxygen dissolves in tissues very rapidly compared to this 5 s interval between images. For example, for a normal, room air inspired breath, it takes ~0.25 s for oxygen to diffuse through a 0.5 µm thick capillary wall and reach its equilibrium with hemoglobin in the pulmonary capillary, a process that includes dissolving in tissue as well as other processes. The process of simple dissolution in tissue thus can be assumed to be complete within this same time frame, as in the exemplary assumption.

FIG. 6 shows illustrations and plots of specific ventilation of an exemplary lung unit model. Illustration (610) and (611) illustrate specific ventilation in the lung unit, in which $V_0$ represents the end-expiratory volume of the unit and $\Delta V$ represents the volume increase that occurs during inspiration in the lung unit. Each voxel (of an MR image) can be simulated as a single ventilatory unit, with end expiratory volume $V_0$, to which inspiration transiently adds $\Delta V$ during each breath (as illustrated in FIG. 6 by illustration (610) and illustration (611)). The initial concentration in the unit at end expiration is denoted $C_0$. $C_n$ (n=1, 2, 3, . . . ) denotes the concentration in the unit at end expiration after breath (n denotes the breath number).

For example, let $C_{insp}^n$ denote the concentration of oxygen in the inspired gas for breath n during the first twenty breaths the subjects are breathing air, (e.g., inspired $F_1O_2=0.21$), and are then changed to a gas mixture enriched in oxygen (e.g., $F_1O_2=1.0$).

At the end of the first breath following the switch in $F_1O_2$, the concentration in the unit is:

$$C_1 = \frac{V_0 \cdot C_0 + \Delta V \cdot C_{insp}^1}{V_0 + \Delta V} \quad (5)$$

The same reasoning can be used to establish a recursive formula for concentration after n breaths:

$$C_n = \frac{V_0 \cdot C_{n-1} + \Delta V \cdot C_{insp}^n}{V_0 + \Delta V} \quad (6)$$

which in turn can be re-written as a function of the unit's specific ventilation, with $SV=\Delta V/V_0$, as:

$$C_n = \frac{1}{1+SV} C_{n-1} + \frac{SV}{1+SV} C_{insp}^n \quad (7)$$

Eq. (7) can be used to model oxygen concentration. A simulated response for an individual voxel can be obtained for a given set of inspired $O_2$ fraction breaths (e.g., inspired oxygen fraction (650), as seen in the dotted line in FIG. 6). For example, FIG. 6 also presents the time series of two units: unit (630) with low specific ventilation (e.g., SV=0.2) and unit (640) with high specific ventilation (e.g., SV=0.8).

A linear relationship can exist between $R=1/T_1$ and $F_1O_2$. The slope and zero crossing values reported for the R1-$F_1O_2$ function can result in a almost linear relationship between $T_1$ and $F_1O_2$ in the range used in the exemplary model and simulation (e.g., $F_1O_2=0.21$ or 1.0).

Based on numerical simulations, for the inversion time described (e.g., 1000 msec) and the variation of T1 with inspired oxygen concentration, the error involved in assuming that the MR signal varies linearly with oxygen concentration is <3% for these exemplary implementations. The calibration curve can be based on this assumption.

Time-Shifted Cross Correlation Between the Driving Function and Simulated Units

To determine the correlation delay time, the cross correlation between each simulated ventilatory unit response and the inspired oxygen fraction can be computed and is represented in FIG. 6 (e.g., simulated ventilatory unit response for unit (630) and unit (640) and inspired oxygen fraction (650)). The inspired $F_1O_2$ curve can be shifted breath-by-breath, and the time shift that maximizes the time-shifted crossed correlation can be a measure of how fast the unit equilibrates, e.g., correlation delay time.

Figure 7A:
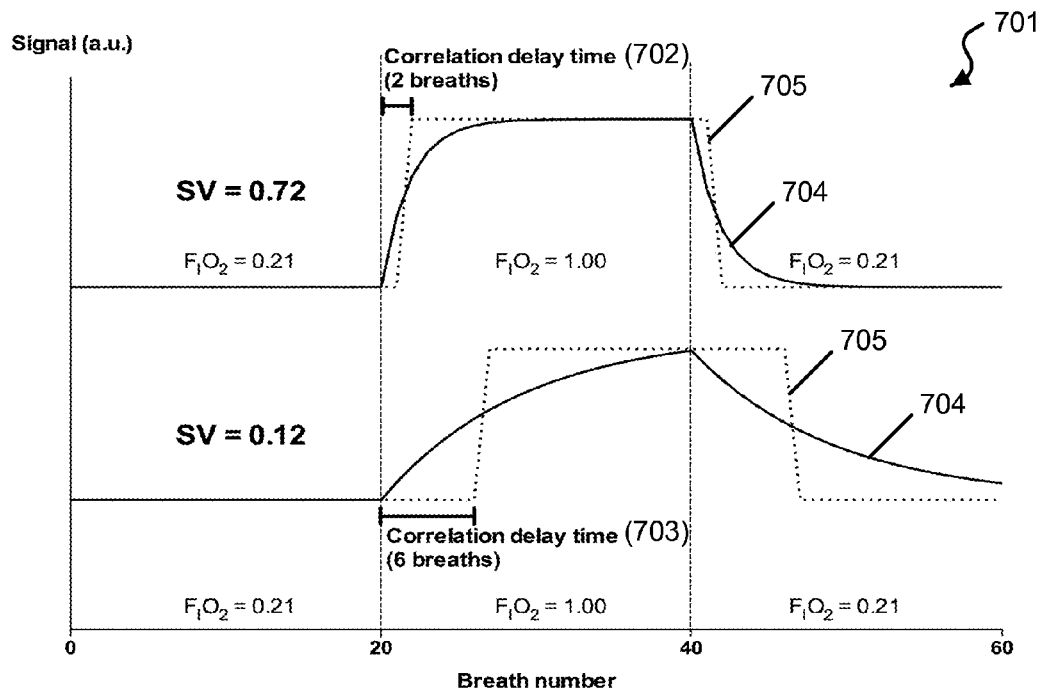
FIG. 7A shows an exemplary plot correlation delay time.

FIG. 7A shows exemplary plot (701) featuring correlation delay time. Correlation delay time can be referred to as the time delay that maximizes the cross-correlation of the measured signal time course from an image voxel with a square wave representing the onset of increased inspired $O_2$. Plot (701) shows two exemplary correlation delay times (correlation delay time (702) for 2 breaths and correlation delay time (703) for 6 breaths) determined based on measured signal time course (704) and rise time (705). Correlation delay time can be used as an empirical measure of the rise time (e.g., rise time (705) shown as dashed lines in FIG. 7A). For example, mathematically, the cross correlation is maximized when the response is shifted by about half the rise time, so that different rise times effectively translate to different delays in the cross-correlation analysis. This allows for the use of correlation delay time as an empirical index of the rise time. This calculation can be done for the entire time series corresponding to each image voxel. It is noted that in some exemplary systems, a dead space, for example, in the plumbing leading from the gas containers to the subject, can introduce a true global delay, but this delay can be calculated from the geometry and flow rate of the delivery system, and eliminated before the cross-correlation analysis.

and the simulated signal was analyzed using the time-shifted cross correlation. The outcome of these exemplary simulations for units with specific ventilation in the range specified is shown in plot (751) of FIG. 7B. Plot (751) can include a conversion tool that allows the translation of correlation delay time (e.g., measured using the proton-MRI acquired time series) into quantitative values of ventilation, on a voxel-per-voxel basis.

Plot (751) shows that for a given measured correlation delay time (shown on the y-axis in FIG. 7B), the corresponding specific ventilation can depend not only on the specific ventilation, but also on an extrinsic delay (for example, which can result from plumbing volume in the inspiratory line, discussed below). In essence, any volume that exists within the experimental configuration between a subject's mouth and the valve used to change between gases of different $F_1O_2$ can introduce a delay that can appear to artificially reduce SV unless, properly accounted for. Thus, it is beneficial to determine this delay by measuring respiratory flow and inspiratory plumbing volume.

Exemplary MRI Data Collection Subjects

In exemplary experiments implementing the exemplary method to quantify specific ventilation (SV), eight healthy subjects (e.g., 3 female, 5 male subjects) were studied in the supine posture. Table 1 presents subject characteristics (e.g., gender, age, height and weight) and pulmonary function data (e.g., $FEV_1$, FVC, and $FEV_1/FVC$). Table 1 shows exemplary subject characteristics, pulmonary function data and slope of the lung height—Specific ventilation relationship for the eight exemplary subjects.

TABLE 1

| Subj | Gndr | Age (yrs) | Ht. (m) | Wt. (kg) | FEV1 (liters) (% predicted) | FVC (liters) (% predicted) | FEV1/FVC (% predicted) | −1/slope (cm$^{-1}$) | Spatial fractal dimension |
|---|---|---|---|---|---|---|---|---|---|
| S1 | M | 33 | 1.81 | 81 | 3.99 88% | 5.17 93% | 0.77 95% | 0.020 | 1.15 |
| S2 | M | 26 | 1.85 | 93 | 4.57 92% | 5.28 87% | 0.87 105% | 0.015 | 1.15 |
| S3 | F | 26 | 1.73 | 68 | 4.13 115% | 5.04 118% | 0.82 96% | 0.031 | 1.15 |
| S4 | F | 39 | 1.62 | 66 | 3.03 101% | 3.65 99% | 0.83 101% | 0.038 | 1.09 |
| S5 | F | 24 | 1.76 | 92 | 3.08 102% | 3.65 99% | 0.84 102% | 0.043 | 1.11 |
| S6 | M | 52 | 1.86 | 113 | 4.50 105% | 5.36 96% | 0.84 109% | 0.046 | 1.10 |
| S7 | M | 34 | 1.78 | 83 | 3.84 89% | 4.98 93% | 0.77 95% | 0.021 | 1.16 |
| S8 | M | 28 | 1.70 | 60 | 4.43 107% | 5.16 103% | 0.86 104% | 0.019 | 1.13 |
| Mean ± SD | | 33 ± 9 | 1.76 ± 0.08 | 82 ± 17 | 3.85 ± 0.61 100 ± 10% | 4.79 ± 0.71 99 ± 9% | 0.82 ± 0.04 101 ± 5% | 0.029* ± 0.012 | 1.13 ± 0.03 |

*Group average significantly different from zero, p = 0.0002.

To relate the correlation delay time to the specific ventilation, an exemplary model of a lung unit can be implemented that simulates the series of consecutive breaths following a sudden change in inspired $F_1O_2$. The simulated data for units with different specific ventilations can be used to calibrate an exemplary signal-processing algorithm, in which the rapidity of the increase/decrease in the MRI signal is measured as a functional delay between the change in $F_1O_2$ and the resulting time course of the MRI signal intensity. The measured functional delay can be translated into quantitative specific ventilation.

Exemplary simulations were performed in units with specific ventilation ranging from 0.05 to 1 in steps of 0.05, MRI Materials and Equipments In exemplary experiments implementing the exemplary method to quantify specific ventilation (SV), MRI data was collected from the exemplary subjects using a 1.5 Tesla Signa HDx TwinSpeed MRI system (e.g., General Electric Medical Systems, Milwaukee, Wis., USA). A single sagittal slice was selected in the right lung, e.g., in order to avoid physiological noise arising from cardiac movements. Slice selection was aimed at selecting the slice within the lung presenting the largest anterior-posterior dimension, while avoiding major hilar vessels.

Exemplary Specific Ventilation Imaging (SVI) Procedures

In exemplary experiments implementing the exemplary method to quantify specific ventilation (SV), two-dimensional $T_1$ weighted images were acquired using an inversion recovery ($T_1$=1000 msec) single shot fast spin echo (SSFSE) sequence, with images being acquired with a half Fourier acquisition (HASTE), and with a 40×40 cm field of view, echo time of approximately 30 ms, and a 15 mm image slice thickness. A MRI homodyne reconstruction algorithm was used to rescale the data to a 256×256 matrix, with each voxel thus corresponding to ~1.6×1.6×15 mm (~40 mm³). An inversion time ($T_1$) of 1000 msec, approximating $T_1$ of lung tissue, was implemented to ensure maximal sensitivity to changes in $O_2$ concentration. The long repetition time used in this single shot fast spin echo sequence (e.g., 5 s, compared to the $T_1$ of blood, 1.4 s) can render the $O_2$ induced contrast independent of lung density. However, lung density does alter the local signal-to-noise ratio. In the exemplary implementations, HASTE acquisition was utilized to keep the echo time short to minimize signal loss observed in the lung. Images were voluntarily respiratory gated. For example, subjects were instructed to take a normal breath in following the noise made by the MR image acquisition, and relax back to Functional Residual Capacity (FRC) at a comfortable expiratory flow rate. Subjects were comfortable with the default 5 s inter-breath intervals (12 breaths per minute). MR images were acquired during a short (e.g., ~hundreds of milliseconds), post-expiratory breath hold at FRC resulting in a relatively natural respiratory maneuver, which was only constrained by a constant breathing rate.

In exemplary experiments implementing the exemplary method to quantify specific ventilation (SV), the addition of $O_2$ as a contrast agent followed a block design functional Magnetic Resonance Imaging (fMRI) approach, which can be utilized for neuroimaging studies. An MR image of a lung was acquired every 5 s, e.g., with 20 images acquired with the subject inspiring air (21% oxygen) and 20 images while inspiring 100% O2. This cycle was repeated 5 times, and an additional 20 breaths of 100% oxygen were added at the end of the last cycle making a total of 220 images (total imaging time was 18 min 20 sec) for an exemplary experiment involving each subject. Blocks of 20 breaths of air and 100% oxygen can ensure an approach to full equilibration for the ranges of specific ventilation and $V_A/Q$ ratios observed in normal healthy subjects. Five cycles of air-oxygen can provide an acceptable signal to noise ratio. While more or less cycles of air-oxygen can be implemented, the exemplary five cycles of air-oxygen were implemented as a compromise between keeping the total acquisition time below 20 min and an improved signal to noise ratio that would result from a longer sequence.

In exemplary experiments implementing the exemplary method to quantify specific ventilation (SV), a face mask (e.g., Hans Rudolph, Kans., USA, with deadspace of 73 to 113 mL, depending on mask size) equipped with a non-rebreathing T-valve (e.g., with deadspace of 27.9 mL) was fitted to the subject. One end of the T-valve was connected to the inlet, where a remote controlled 3-way pneumatic sliding valve (e.g., Hans Rudolph, model 8500) allowed rapid switching between room air and $O_2$ contained in a 170 liter Douglas bag (e.g., Hans Rudolph type 6170). The inspiratory path resistance on the room air and $O_2$ circuits were matched to eliminate changes in FRC following changes in inspiratory path. The outlet of the T-valve was connected to a ~6 m long large bore low resistance expiratory line, leading out of the scanner room, where expired tidal volume was simultaneously measured using a Parvo-Medics Metabolic Measurement System (ParvoMedics, Sandy, Utah, USA).

The exemplary experimental configuration for controlling the inspired gas (room air, 100% oxygen) introduced an extrinsic plumbing delay in the inspired signal that can be determined by the volume of tubing that connects the remote control valve to the subject. This volume was made as small as possible (e.g., 0.6 L) under constraints imposed by working in an MRI environment. Neglecting diffusion, this delay can be computed from each subject's tidal volume and the tubing volume, by dividing the tubing volume by the tidal volume. For example, in practice, this extrinsic delay can be taken into account by computing individual inspired fractional oxygen concentration ($F_1O_2$) time series on a breath-by-breath basis (e.g., $C_{insp}^2$ in Eq. (7)), taking the tubing volume as a delay chamber of fixed volume, through which the inspired gas must pass. Once this extrinsic plumbing delay is corrected for, what is left corresponds to the signal intensity change over time, allowing the computation of specific ventilation as described in the next section.

Exemplary Specific Ventilation Imaging (SVI) Data Analysis

In exemplary experiments implementing the exemplary method to quantify specific ventilation (SV), a time series of the exemplary 220 images corresponding to the SVI sequence was constructed. Quality control of the acquired image can be performed at this stage. For example, images in which a subject was not at FRC based on diaphragm position compared to adjacent images can be removed from the series and replaced by an interpolated image, constructed from the preceding and following images. In exemplary experiments, a region of interest was manually drawn, and the subsequent analyses were restricted to the voxels inside the lung. For example, the region of interest encompassed the entire lung, yet avoided partial volume effects from regions close to the chest wall and the diaphragm. Data analysis was performed on a voxel-by-voxel basis, the time course of each voxel (e.g., MRI signal intensity versus time) was used to compute the regional correlation delay time. For example, data analysis can be performed using Matlab software (Mathworks, Natick, Mass.).

In exemplary experiments implementing the exemplary method to quantify specific ventilation (SV), the correlation delay time was computed using a shifted cross correlation between the inspired $F_1O_2$ and the acquired signal intensity time series. The time shifted cross correlation can be considered as a fast and simple approach to implement, fitting only one parameter (e.g., the correlation delay time), and is independent of the asymptotic signal intensity. For example, by removing this extra degree of freedom, the model can remain simple while capturing only the time course of the transition. This can leave out, for example, the physiological dead space, water vapor, ratios; factors that alter the steady state $CO_2$ concentration, and any effect of varying $V_A/Q$ concentration, but not the time course of the transition. Moreover, the shifted correlation delay approach can act as a smoothing low pass filter, eliminating some of the high frequency noise present in the exemplary data that did not allow a direct fit of the model (Eq. (7)). In practice, for example, the inspired $F_1O_2$ (driving function) can be correlated with the time course of each voxel, and this process can be repeated for delayed versions of the driving function (e.g., delayed by an integer or fractional number of breaths). The delay that maximizes the cross correlation between the time shifted driving function and the actual voxel response is the correlation delay time. The correlation delay time computed in this exemplary way can retain voxels whose correlation with the optimal shifted inspired fractional oxygen concentration is significant (P<0.05), and the null hypothesis of no correlation can be rejected in these cases. In voxels in which the null hypothesis is accepted, the corresponding lung voxel can be attributed no specific ventilation value and treated as missing data.

Figure 8:
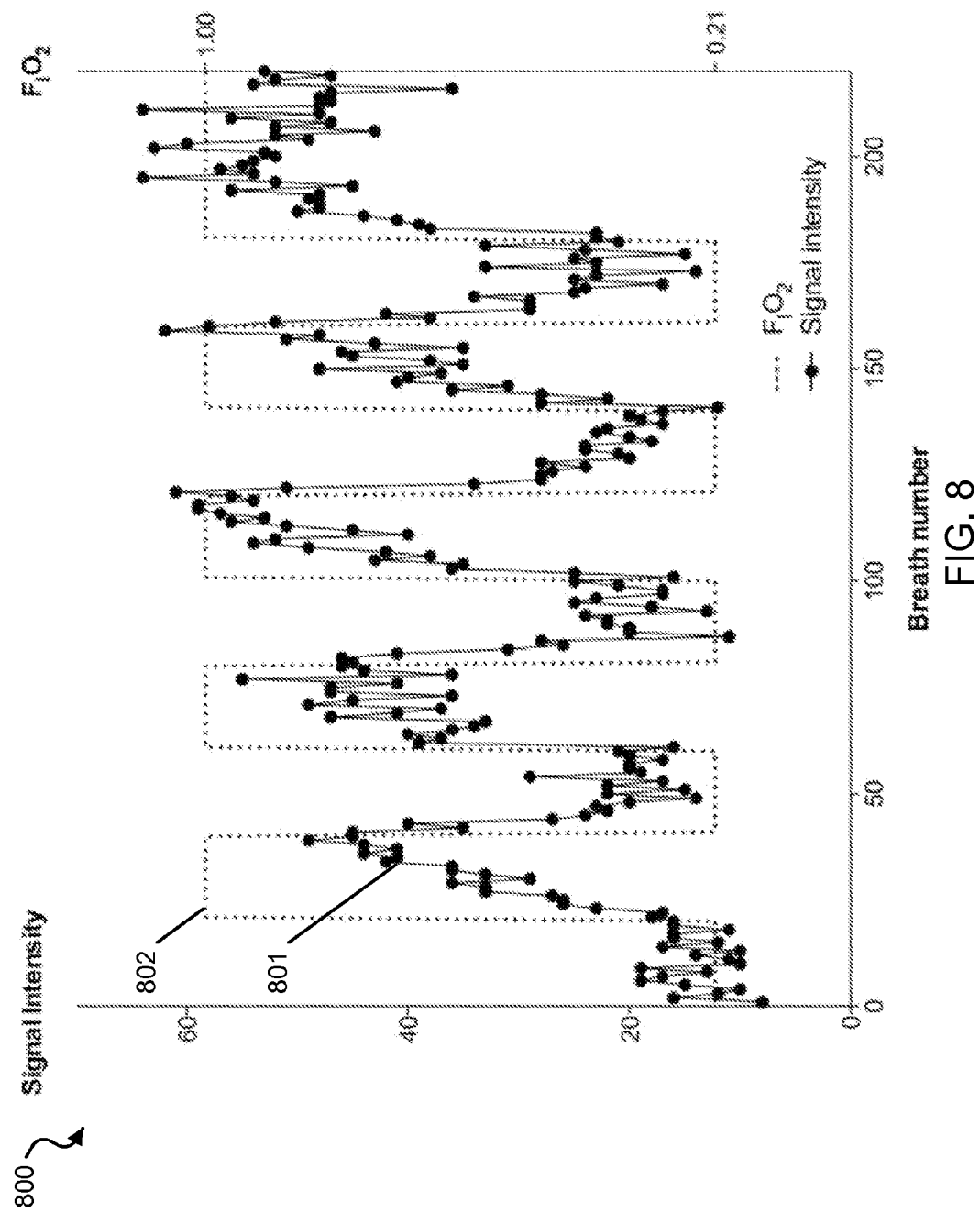
FIG. 8 shows an exemplary time series of signal intensity for a single voxel.

FIG. 8 shows an exemplary time course plot (800) of signal intensity (801), represented by filled circles, continuous lines) for one such exemplary voxel. The arbitrarily chosen exemplary voxel plotted was located in the dependent portion of the lung. The corresponding driving function (802) representing $F_IO_2$ is also shown, represented by the dotted line. The delay between the driving function and the measured signal intensity is a measure of the correlation delay time for that voxel.

Exemplary Statistical Analyses

In exemplary experiments implementing the exemplary method to quantify specific ventilation (SV), each series of 220 breaths was considered as a single measure of specific ventilation, computed as described above, creating for each subject one map of specific ventilation. All the voxels presenting a statistically significant (p<0.05) correlation with the optimally shifted drive function were included in the exemplary analysis. The remaining voxels were treated as missing data. Two different exemplary analyses were implemented, e.g., a comparison of specific ventilation by lung thirds and a finer analysis on a cm-per-cm basis moving up the supine lung.

For the exemplary lung thirds analysis, specific ventilation was partitioned into three gravitational regions, corresponding to thirds of the lung based on equal vertical extent, e.g., the dependent portion, the intermediate region, and the non-dependent region. The data was reduced to a subject-by-subject average specific ventilation per lung gravitational region. One-way ANOVA was used to compare the gravitational gradient in specific ventilation across the lung regions (e.g., the 3 levels: dependent, intermediate, and non-dependent). Where overall significance was present, post-hoc testing was conducted using Student's t-test.

For the exemplary finer analysis (cm-per-cm basis moving up the supine lung), linear regression was used to evaluate the linear relationship between the vertical height of the lung as a function of specific ventilation, e.g., by dividing the data into isogravitational slices of 1 cm thickness (~6 vertical voxels). As the exemplary subjects were studied in the supine position, the vertical height of the lung (isogravitational level) was measured along the anterior-posterior axis, with zero height corresponding to the most dependent isogravitational voxels. The linear relationships were evaluated individually for each subject. The inter-subject averaged specific ventilation versus lung height values correspond to averages over vertical 1 cm regions for the 8 subjects.

It is noted that different subjects have different anterio-posterior lung dimensions; therefore, results were reported only for lung heights that included data from the eight subjects. The slope of the individual relationships between height and specific ventilation were compared to a zero slope using a one-group t-test.

It is noted that exemplary data are presented as mean±SD. In the case in which data for the eight subjects were averaged, SD corresponds to the inter-subject variability (SD). Regarding the calculating relative dispersion, spatial SD refers to the inter-voxel variability within a specific ventilation map. The null hypothesis (no effect) was rejected when P<0.05, two tailed, except where otherwise indicated.

Exemplary statistical analyses were performed using Prism (GraphPad, San Diego, Calif.).

Exemplary Results

General results of the exemplary experiments implementing the exemplary method to quantify specific ventilation (SV) included the following. Subject descriptive data and pulmonary function measurements are presented in Table 1. The subjects studied in the exemplary experiments had normal spirometry, as indicated by an average $FEV_1$=100±10%-predicted, FVC=99±9%-predicted, and $FEV_1$/FVC=101±5%-predicted (as shown in Table 1). The exemplary subjects maintained a relatively constant expired tidal volume throughout the experiment, e.g., averaging 0.87±0.18 L. Heart rate during SVI data acquisition averaged 65±9 beats/min (e.g., no difference between inspiring air and 100% oxygen), and arterial oxygen saturation measured by pulse oximetry was 97.4±1.7% while breathing room air and increased to 97.8±1.5% during inspiration of 100% oxygen. The selected breathing rate was followed by all subjects in the exemplary experiments, and tidal volume was relatively stable throughout the 220 breaths (e.g., the average CV for the eight subjects was 16%). Tidal volume did not change when comparing breaths taken while inspiring air and oxygen (e.g., average over the eight exemplary subjects, 0.86±0.15 Liters on air, 0.87±0.17 Liters, 2-tailed t-test paired comparison, p=0.82).

SVI results of the exemplary experiments implementing the exemplary method to quantify specific ventilation (SV) included the following. FIG. 8 presents the time series (e.g., time course plot (800)) of the signal intensity of a voxel (e.g., signal intensity (801)) together with the inspired $F_IO_2$ (function (802)) for a voxel in the dependent lung region. The exemplary experiment included five repetitions of a block of 20 air breaths and 20 100%-oxygen breaths performed by a subject. As shown in the figure, when the inspired line was changed from air to 100% oxygen, signal intensity increased; signal intensity decreased for the opposite change, e.g., from 100% oxygen back to room air. After the 5 cycles of air and 100% oxygen, twenty additional breaths on 100% oxygen were added in the exemplary experiment. Noise can be expressed as the coefficient of variation of the steady state signal (e.g., first 20 breaths on air, and last 20 breaths inspiring $O_2$) averaged over the entire lung of the 8 subjects studies. The exemplary noise was determined as 22.8±1.5% for air, and 18.4±1.8% for oxygen. In order to test the robustness of the exemplary algorithm, the disclosed model was run with similar levels of random noise. The average specific ventilation estimation error introduced by 20% noise levels can be considered as extremely small (e.g., average error in estimating SV ~0.003). The maximal SV estimation error was determined to be ~0.013 and was observed for very low specific ventilation units (SV<0.02), e.g., which is below the normal healthy range.

Figure 9A:
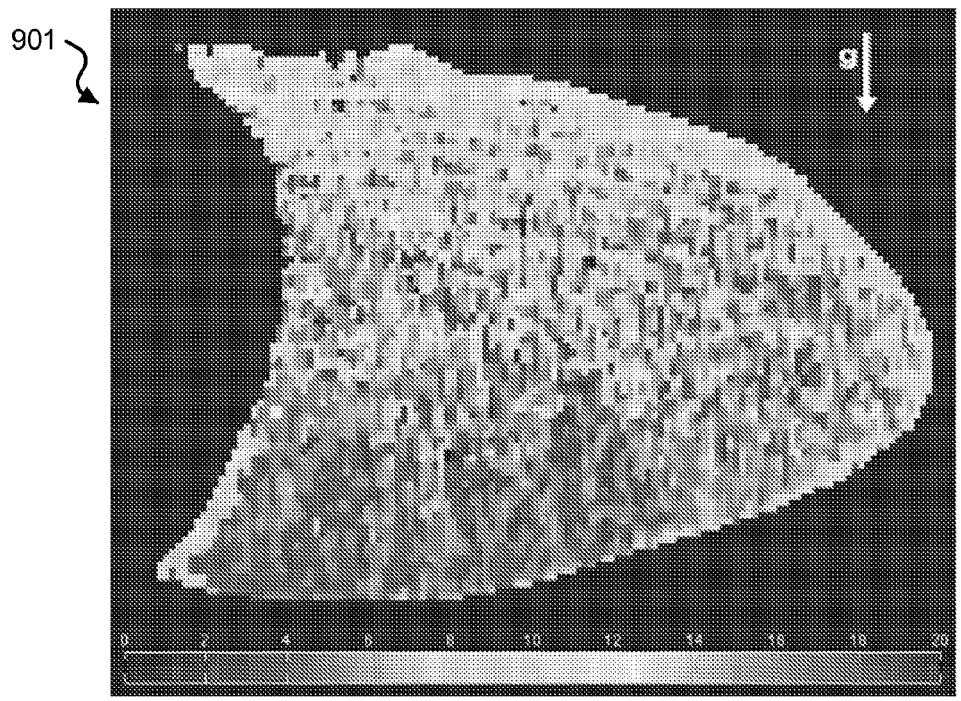
FIG. 9A shows an exemplary correlation delay time map in a sagittal slice of the lung.

From each individual voxel response, a map of the correlation delay time for all voxels within the lung can be computed. An exemplary individual voxel response maps is presented for a representative subject, as shown by map (901) in FIG. 9A. The arrow shown indicates the direction of gravity; the head is located to the right of the image, and the diaphragm to the left. In FIG. 9A, warmer colors (e.g., colors trending toward red) represent portions of the lung with a longer correlation delay time. As previously discussed, the extrinsic delay resulting from the inspiratory plumbing was accounted for prior to the analysis.

Figure 7B:
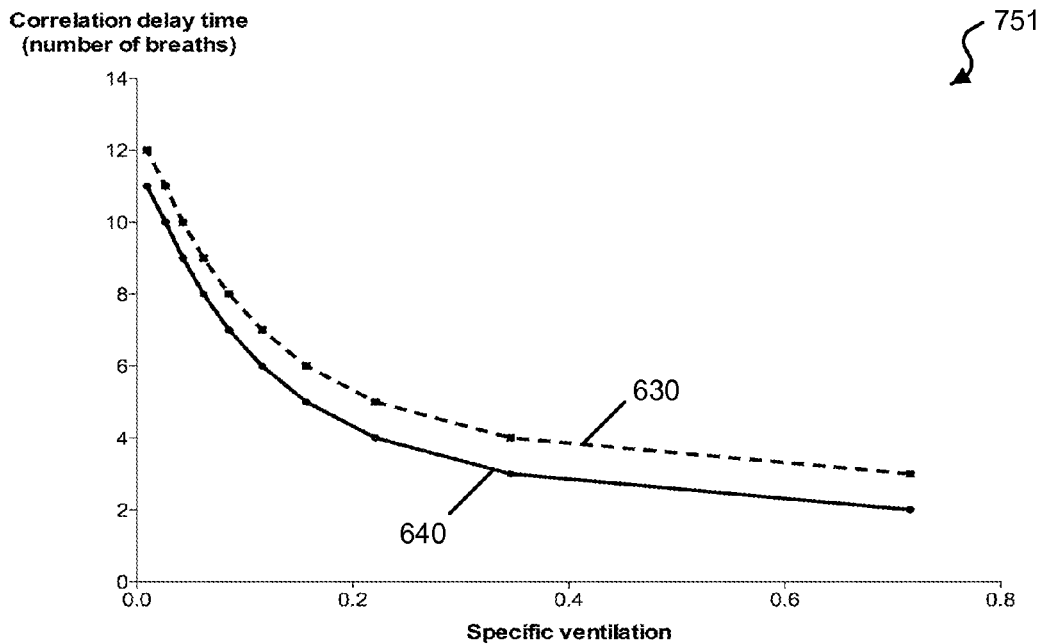
FIG. 7B shows an exemplary plot of the relationship of correlation delay to specific ventilation.
Figure 9B:
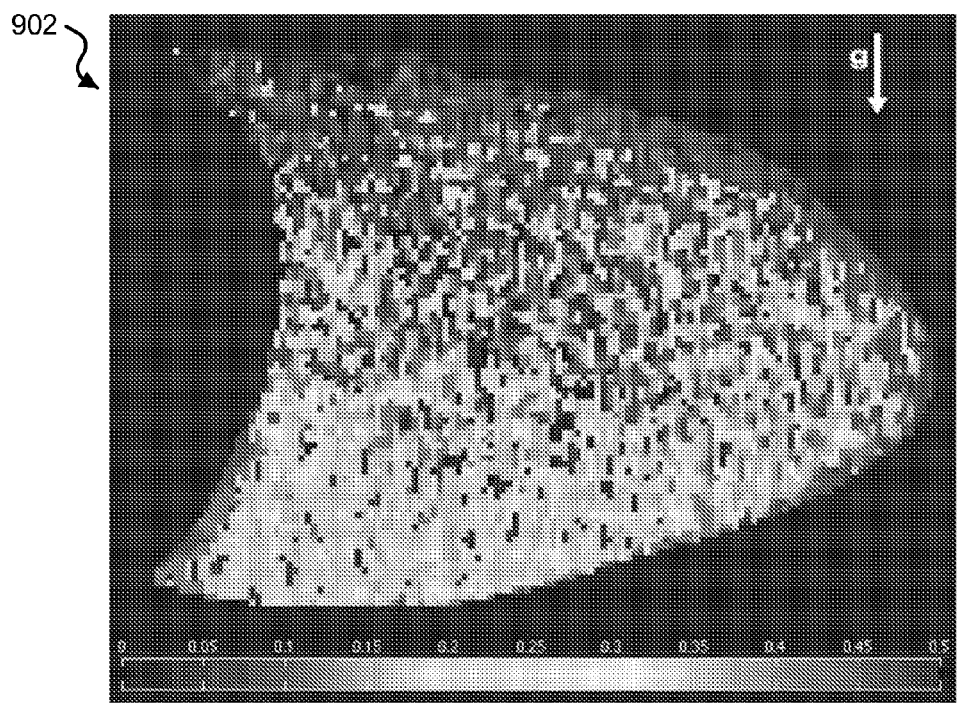
FIG. 9B shows an exemplary corresponding specific ventilation map.

Using the results presented in FIG. 7B, this correlation delay time was then translated into a quantitative measure of specific ventilation, as shown by map (902) in FIG. 9B. In FIG. 9B, warmer colors (e.g., colors trending toward red) represent regions of the lung with higher specific ventilation. The quantitative measure of specific ventilation results of the exemplary experiments implementing the disclosed technology include average specific ventilation in a slice of the right lung (averaged over all subjects) determined to be 0.33±0.11. Overall specific ventilation heterogeneity, as measured by the relative dispersion, averaged 0.63±0.11; with an individual range of 0.50 to 0.79.

The exemplary results of quantitative measure of specific ventilation as shown in FIG. 9B demonstrates a clear vertical (gravitational) gradient of specific ventilation is present. Units in the dependent portions of the lung have higher specific ventilation than those in the non-dependent portions of the lung. This relationship is quantified in graph (1000) of FIG. 10, which is shown in the results for the regional dependence of specific ventilation over the eight exemplary subjects in the three regions, e.g., nondependent region (1001), intermediate region (1002) and dependent region (1003). For example, a statistically significant difference in specific ventilation was observed, with the most dependent third of the lung having a specific ventilation of 0.42±0.14, the intermediate third 0.29±0.10 and the non-dependent third 0.24±0.08 (all differences, P<0.05).

Figure 11A:
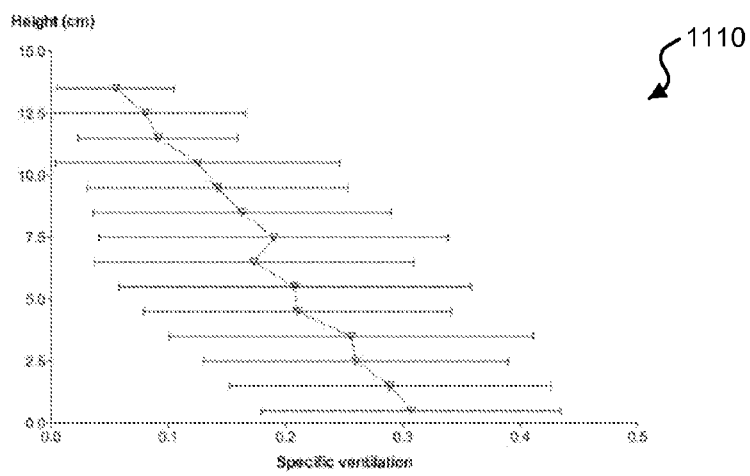
FIGS. 11A, 11B, and 11C show exemplary graphs of specific ventilation plotted versus the vertical distance from the most dependent portion of the lung.
Figure 11B:
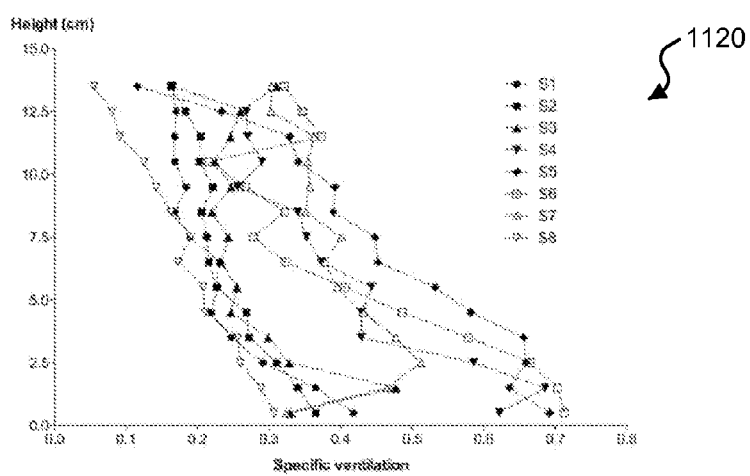
Figure 11C:
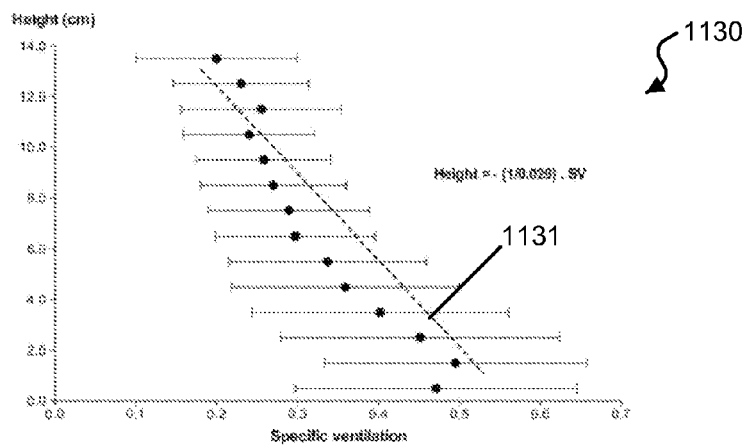

An approximately linear decrease in specific ventilation with height was observed, as evidenced in FIGS. 11A-11C. FIG. 11A shows specific ventilation plotted against height for one exemplary subject in plot (1110). FIG. 11B shows specific ventilation plotted against height for each of the eight exemplary individual subjects in plot (1120). FIG. 11C shows the average specific ventilation plotted against height of all eight exemplary subjects in plot (1130). The inverse of the slope of the plotted line shown in FIGS. 11A-11C is a measure of the decrease in specific ventilation per cm. Specific ventilation was found to decrease 0.029±0.012/cm on average for the eight exemplary individual subjects, determined from the inverse of the (slope 1131) shown in FIG. 11C.

The exemplary implementation of the disclosed $O_2$-enhanced proton MR imaging technology showed regional quantification of specific ventilation, which can, for example, extract more information than just absence or presence of ventilation. For example, from a physiological standpoint, specific ventilation imaging (SVI) can show a clear vertical (gravitational dependent) gradient with higher values, which was demonstrated in the exemplary experiments as shown in dependent lung in FIG. 10.

The spring like self-deformation of the lung, e.g., the Slinky effect, is likely the main determinant of the gravitational gradient observed in specific ventilation. However, in the most dependent third of the supine lung there are deviations from this overall behavior suggesting important influences of other factors such as the non-linearity of the pressure-volume curve of the lung, the large vessels in the lung, and dependent airways closure.

Figure 10:
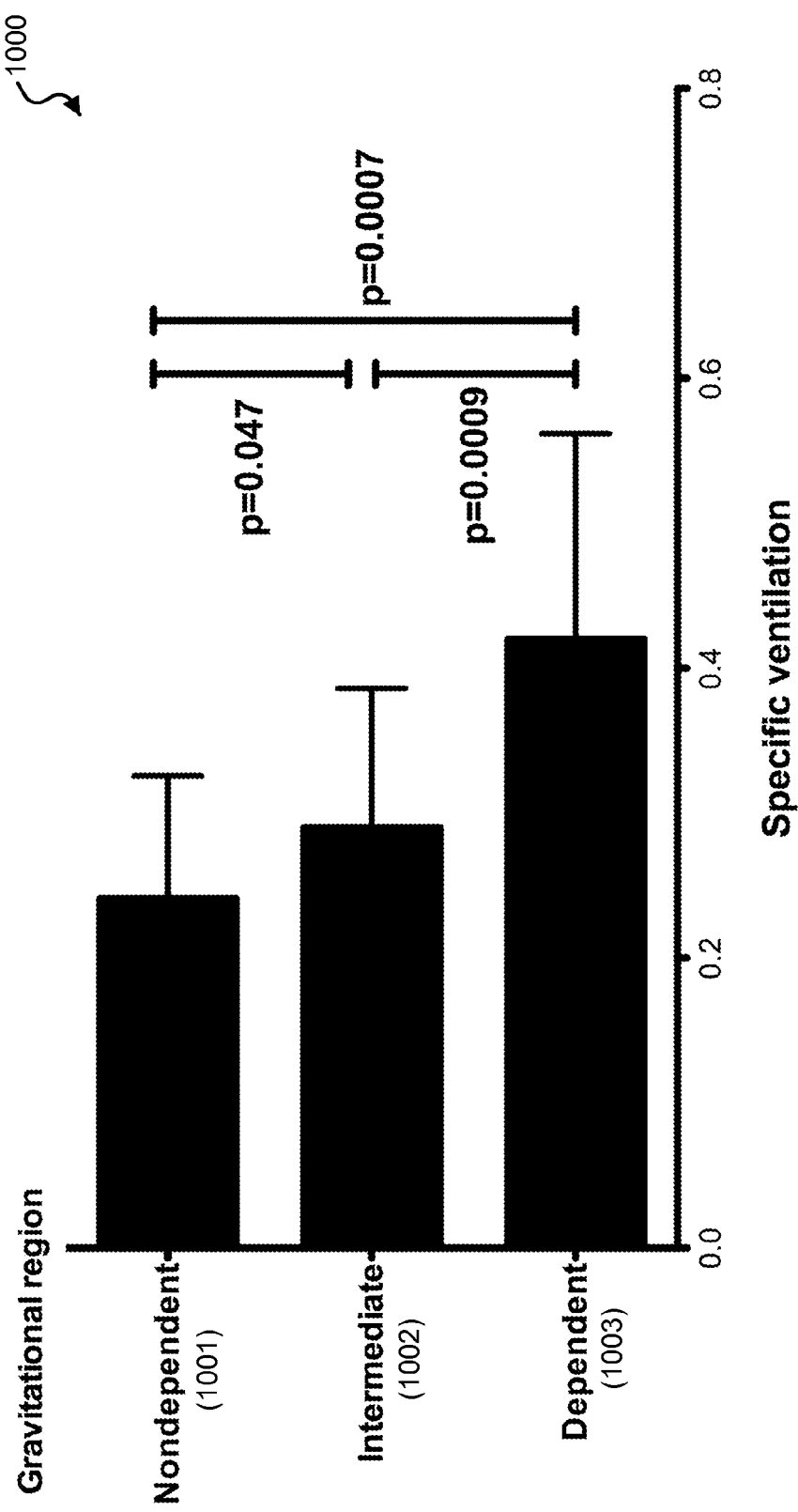
FIG. 10 shows an exemplary graph of specific ventilation for each lung region.

The exemplary measurements show a linear vertical gradient in specific ventilation (FIGS. 9A-4C and 11A and 11B). Dependent portions of the lung have a higher specific ventilation that the non-dependent portions (FIG. 10). The dependent portion of the lung partially supports the weight of the upper portions, and thus is more "compressed." Therefore its end-expiratory volume is smaller. Further, the dependent portion is subject to a higher (less negative) pleural pressure than an equivalent non-dependent region, therefore placing it on a steeper portion of the pressure-volume curve. For example, a change in pleural pressure resulting from an inspiratory effort may result in a greater increase in volume. Both the lower initial (end-expiratory) volume and the increased change in volume can be expected to contribute to the higher specific ventilation observed in the dependent regions of the lung, when compared to the non-dependent.

Quantification of specific ventilation in the human lung can be implemented by the described method of proton-MRI SVI, which uses $O_2$ as an inspired contrast agent.

Implementations of the subject matter and the functional operations described in this specification can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non volatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Only a few implementations and examples are described and other implementations, enhancements and variations can be made based on what is described and illustrated in this patent document.

What is claimed is:

1. A computer-implemented method using magnetic resonance imaging to characterize ventilation and perfusion in a lung, comprising:
    acquiring, using a magnetic resonance imaging (MM) machine under the control of a processing unit, a magnetic resonance (MR) image of the lung that includes MR data in a voxel of the MR image, wherein the acquiring causes the MM machine to measure a breathing frequency value;
    determining, by the processing unit a water density value and a perfusion value in at least one voxel of the MR image based on the MR data;
    determining, by the processing unit from the water density value, an air content value in the at least one voxel;
    determining, by the processing unit, a specific ventilation value in the at least one voxel based on a time delay between an onset of a stimulus to the lung and a response detected in the at least one voxel;
    determining, by the processing unit a ventilation-perfusion ratio value that is the product of the specific ventilation value, the air content value, the inverse of the perfusion value, and the breathing frequency value; and
    evaluating, by the processing unit, a spatial distribution of the specific ventilation value, perfusion value, and the ventilation-perfusion ratio by computing a standard deviation of the specific ventilation value and perfusion value;
    wherein the specific ventilation value is computed by $SVI*(1-density)*f_B$ wherein SVI represents quantitative data from the MR image, (1−density) represents the air content value, and $f_B$ represents the breathing frequency value, thereby determining when the lung is diseased.

2. The method of claim 1, wherein the MR image is a 2D image or a 3D image.

3. The method of claim 1, wherein the determining the ventilation-perfusion ratio value is determined voxel-by-voxel.

4. The method of claim 1, wherein the acquiring the MR image uses oxygen as an inhaled contrast agent.

5. The method of claim 1, further comprising determining an alveolar ventilation value that is the product of the specific ventilation value, the air content value, and the breathing frequency value.

6. The method of claim 5, further comprising:
    computing a first variance in the specific ventilation value, a second variance in the perfusion value, and a third variance in the ventilation-perfusion ratio value; and
    generating a correlation coefficient from one or more of the first variance, the second variance, and the third variance.

7. The method of claim 1, further comprising producing an image that shows the spatial distribution of ventilation, perfusion, and ventilation-perfusion for each voxel associated with the acquired MR image.

8. The method of claim 1, wherein the spatial distribution of ventilation, perfusion, and ventilation-perfusion is used as an indicator of a diseased lung.

9. The method of claim 1, further comprising:
    determining ventilation-perfusion matching in the lung from at least the ventilation-perfusion ratio value.

10. The method of claim 9, wherein ventilation-perfusion matching is used as an indicator of a diseased lung.

11. A magnetic resonance imaging system to characterize ventilation and perfusion in a lung, comprising:
    a magnetic resonance imaging machine that acquires an MR image of the lung; and
    a processing unit having a processor and a non-transitory computer-readable storage medium having instructions stored thereon that when executed by the processor cause the processing unit to at least:
    command the magnetic resonance imaging machine to acquire the MR image that includes MR data in each voxel of the MR image,
    process the MR data to determine a water density value and a perfusion value in at least one voxel of the MR image, wherein the water density value is used to determine an air content value,
    measure a breathing frequency of the lung;
    determine a specific ventilation value in the at least one voxel based on a time delay between an onset of a stimulus to the lung and a response detected in the at least one voxel;
    determine a ventilation-perfusion ratio value that is the product of the specific ventilation value, the air content value, the inverse of the perfusion value, and the breathing frequency; and
    evaluate a spatial distribution of the specific ventilation value, perfusion value, and the ventilation-perfusion ratio by computing a standard deviation of the specific ventilation value and perfusion value;

wherein the specific ventilation value is computed by SVI*(1−density)*$f_B$ wherein SVI represents quantitative data from the MR image, (1−density) represents the air content value, and $f_B$ represents the breathing frequency value, thereby determining when the lung is diseased.

12. The magnetic resonance imaging system of claim 11, wherein the MRI system uses oxygen as an inhaled contrast agent to acquire the MR image of the lung.

13. The magnetic resonance imaging system of claim 11, wherein the instructions, when executed by the processor, further cause the processing unit to at least:

determine an alveolar ventilation value that is the product of the specific ventilation value, the air content value, and the breathing frequency.

14. The magnetic resonance imaging system of claim 13, wherein the instructions, when executed by the processor, further cause the processing unit to at least:

compute a first variance in the specific ventilation value, a second variance in the perfusion value, and a third variance in the ventilation-perfusion ratio; and generating a correlation coefficient from one or more of the first variance, the second variance, and the third variance.

15. The magnetic resonance imaging system of claim 11, wherein the instructions, when executed by the processor, further cause the processing unit to at least:

produce an image that shows the spatial distribution of ventilation, perfusion, and ventilation-perfusion for each voxel associated with the acquired MR image.

16. The magnetic resonance imaging system of claim 11, wherein the processing unit uses the spatial distribution of ventilation, perfusion, and ventilation-perfusion as an indicator of a diseased lung.

17. The magnetic resonance imaging system of claim 11, wherein the instructions, when executed by the processor, further cause the processing unit to at least:

determine ventilation-perfusion matching in the lung from at least the ventilation-perfusion ratio value.

18. The magnetic resonance imaging system of claim 17, wherein the processing unit uses ventilation-perfusion matching as an indicator of a diseased lung.

19. A computer program product comprising a non-transitory computer-readable storage medium having instructions stored thereon, the instructions comprising:

code for acquiring, using a magnetic resonance imaging (MRI) machine, an MR image of a lung that includes MR data in a voxel of the MR image;

code for determining a water density value and a perfusion value in at least one voxel of the MR image based on the MR data, wherein the water density value is used to determine an air content value;

code for measuring a breathing frequency value;

code for determining a specific ventilation value in the at least one voxel based on a time delay between an onset of a stimulus to the lung and a response detected in the at least one voxel;

code for determining a ventilation-perfusion ratio value that is the product of the specific ventilation value, the air content value, the inverse of the perfusion value, and the breathing frequency value; and code for evaluating a spatial distribution of the specific ventilation value, perfusion value, and the ventilation-perfusion ratio by computing a standard deviation of the specific ventilation value and perfusion value, wherein the specific ventilation value is computed by SVI*(1−density)*$f_B$ wherein SVI represents quantitative data from the MR image, (1−density) represents the air content value, and $f_B$ represents the breathing frequency value, thereby determining when the lung is diseased.

20. The non-transitory computer-readable storage medium of claim 19, wherein the code for acquiring the MRI image of the lung includes code that uses oxygen as an inhaled contrast agent.

21. The non-transitory computer-readable storage medium of claim 19, further comprising code for determining an alveolar ventilation value that is the product of the specific ventilation value, the air content value, and the breathing frequency.

22. The non-transitory computer-readable storage medium of claim 21, wherein code for determining the alveolar ventilation value includes code for computing a first variance in the specific ventilation value, a second variance in the perfusion value, and a third variance in the ventilation-perfusion ratio; and generating a correlation coefficient from one or more of the first variance, the second variance, and the third variance.

23. The non-transitory computer-readable storage medium of claim 19, wherein code for determining the alveolar ventilation value further comprises code for producing an image that shows the spatial distribution of ventilation, perfusion, and ventilation-perfusion for each voxel associated with the acquired MR image.

24. The non-transitory computer-readable storage medium of claim 19, wherein code for determining the alveolar ventilation value further comprises code for using the spatial distribution of ventilation, perfusion, and ventilation-perfusion to indicate a diseased lung.

25. The non-transitory computer-readable storage medium of claim 19, further comprising code for determining ventilation-perfusion matching in the lung from at least the ventilation-perfusion ratio value.

26. The non-transitory computer-readable storage medium of claim 25, wherein code for determining ventilation-perfusion matching further comprises code for using ventilation-perfusion matching to indicate a diseased lung.

* * * * *